(12) United States Patent
Kim et al.

(10) Patent No.: US 8,338,148 B2
(45) Date of Patent: Dec. 25, 2012

(54) **METHOD OF PRODUCING 1,3-PROPANEDIOL USING RECOMBINANT *KLEBSIELLA* STRAIN IN WHICH GLYCEROL OXIDATIVE PATHWAY HAS BEEN BLOCKED**

(75) Inventors: Chul-Ho Kim, Daejeon (KR); Jeong-Woo Seo, Seoul (KR); Baek Rock Oh, Gwangju (KR); Sun-Yeon Heo, Jeollabuk-do (KR); Mi Young Seo, Jeollanam-do (KR); Min Ho Choi, Chungcheongbuk-do (KR); Jin-Oh Baek, Daejeon (KR); Pil-Soo Seo, Busan (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/148,307

(22) PCT Filed: Mar. 12, 2009

(86) PCT No.: PCT/KR2009/001236
§ 371 (c)(1),
(2), (4) Date: Sep. 21, 2011

(87) PCT Pub. No.: WO2010/104224
PCT Pub. Date: Sep. 16, 2010

(65) Prior Publication Data
US 2012/0045808 A1 Feb. 23, 2012

(51) Int. Cl.
*C12P 7/18* (2006.01)
*C12P 7/14* (2006.01)
*C12N 1/20* (2006.01)

(52) U.S. Cl. ............... 435/158; 435/162; 435/252.3

(58) Field of Classification Search .......... None
See application file for complete search history.

(56) References Cited

U.S. PATENT DOCUMENTS

| | | | |
|---|---|---|---|
| 3,687,981 A | 8/1972 | Lawrence et al. |
| 5,015,789 A | 5/1991 | Arntz et al. |
| 5,254,467 A | 10/1993 | Kretschmann et al. |
| 2005/0079617 A1 | 4/2005 | Cervin et al. |
| 2006/0121581 A1 | 6/2006 | Cervin et al. |
| 2007/0072279 A1 | 3/2007 | Meynial-Salles et al. |
| 2009/0142843 A1 | 6/2009 | Cervin et al. |

FOREIGN PATENT DOCUMENTS

| KR | 10-2005-0088072 A | 9/2005 |
|---|---|---|
| KR | 10-2006-0123490 A | 12/2006 |
| KR | 10-2007-0121282 A | 12/2007 |
| KR | 10-2008-0122166 | 6/2010 |
| WO | WO 93/25696 A1 | 12/1993 |
| WO | WO 2008/052595 A1 | 5/2008 |
| WO | WO 2010/064744 A1 * | 6/2010 |

OTHER PUBLICATIONS

Forage et al., J. Bacteriol. 151:591-599, 1982.*
Cheng et al., Process Biochem. 42:740-744, 2007.*
Kemmerich et al., Antimicrobial Agents and Chemotherapy 31:417-420, 1987.*
Matsuo et al., Clin. Chem. 29:1912-1915, 1983.*
Huang et al., Appl. Biochem. Biotechnol. 98-100:687-698, 2002.*
Zhang et al., Metabolic Engineer. 8:578-586, 2006.*
Yang et al., Appl. Microbiol. Biotechnol. 73:1017-1024, 2007.*
Gonzalez-Pajuelo et al., Appl. Environ. Microbiol. 72:96-101, 2006.*
Tong et al., Appl. Environ. Microbiol. 57:3541-3546, 1991.*
Bachler et al., EMBO J. 24:283-293, 2005.*
English Language Abstract of KR 10-2005-0088072 A, Sep. 1, 2005.
English Language Abstract of KR 10-2006-0123490 A, Dec. 1, 2006.
English Language Abstract of KR 10-2007-0121282 A, Dec. 27, 2007.
English Language Abstract of KR 10-2010-0063585 A which is the application publication of KR 10-2008-0122166, Jun. 11, 2010.
International Search Report for PCT/KR2009/001236 mailed on Dec. 16, 2009.

\* cited by examiner

*Primary Examiner* — David J Steadman
(74) *Attorney, Agent, or Firm* — Rabin & Berdo, P.C.

(57) ABSTRACT

Provided is a method of producing 1,3-propanediol by culturing a recombinant strain in which the glycerol oxidative pathway had been blocked, and more particularly a method of producing 1,3-propanediol by two-step culture of a recombinant strain in which the oxidative pathway that produces byproducts in the glycerol metabolic pathway had been blocked. When the recombinant strain in which the glycerol oxidative pathway that produces byproducts had been blocked is cultured in two steps, 1,3-propanediol can be produced with improved yield without producing products that result in an increase in purification costs.

16 Claims, 16 Drawing Sheets

A

B

```
SEQUENCE LISTING

<160> NUMBER OF SEQ ID NOS: 14

<210> SEQ ID NO 1
<211> LENGTH: 27
<212> TYPE: DNA
<213> ORGANISM: Artificial
<220> FEATURE:
<223> OTHER INFORMATION: primer

<400> SEQUENCE: 1
tctagaatga aaagatcaaa acgattt                                       27
```

```
<210> SEQ ID NO 2
<211> LENGTH: 24
<212> TYPE: DNA
<213> ORGANISM: Artificial
<220> FEATURE:
<223> OTHER INFORMATION: primer

<400> SEQUENCE: 2
ggatccgtca gcggcaatct gcac                                             24

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
aagcttcatg ctctccggcg cctgtc                                           26

<210> SEQ ID NO 4
<211> LENGTH: 28
<212> TYPE: DNA
<213> ORGANISM: Artificial
<220> FEATURE:
<223> OTHER INFORMATION: primer

<400> SEQUENCE: 4
agatctattt ggtccagcga gctgaagc                                         28

<210> SEQ ID NO 5
<211> LENGTH: 26
<212> TYPE: DNA
<213> ORGANISM: Artificial
<220> FEATURE:
<223> OTHER INFORMATION: primer

<400> SEQUENCE: 5
agatctcctg ggatttcgcg acggca                                           26

<210> SEQ ID NO 6
<211> LENGTH: 27
<212> TYPE: DNA
<213> ORGANISM: Artificial
<220> FEATURE:
<223> OTHER INFORMATION: primer

<400> SEQUENCE: 6
aagctttcga caatcggttt taaggtg                                          27

<210> SEQ ID NO 7
<211> LENGTH: 26
<212> TYPE: DNA
<213> ORGANISM: Artificial
<220> FEATURE:
<223> OTHER INFORMATION: primer

<400> SEQUENCE: 7
gttaacctga cgccgttgga tacacc                                           26

<210> SEQ ID NO 8
<211> LENGTH: 32
<212> TYPE: DNA
<213> ORGANISM: Artificial
<220> FEATURE:
<223> OTHER INFORMATION: primer
```

<400> SEQUENCE: 8
agatctaaaa gcttatgagc tcagccaatc ga                                32

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9
agatctatga gctatcgtat gtttga                                       26

<210> SEQ ID NO 10
<211> LENGTH: 32
<212> TYPE: DNA
<213> ORGANISM: Artificial
<220> FEATURE:
<223> OTHER INFORMATION: primer

<400> SEQUENCE: 10
ctcgagaagc ttcagaatgc ctggcggaaa at                                32

<210> SEQ ID NO 11
<211> LENGTH: 27
<212> TYPE: DNA
<213> ORGANISM: Artificial
<220> FEATURE:
<223> OTHER INFORMATION: primer

<400> SEQUENCE: 11
agatctatga acaactttaa tctgcac                                      27

<210> SEQ ID NO 12
<211> LENGTH: 26
<212> TYPE: DNA
<213> ORGANISM: Artificial
<220> FEATURE:
<223> OTHER INFORMATION: primer

<400> SEQUENCE: 12
agatctatga ataatttcga cctgca                                       26

<210> SEQ ID NO 13
<211> LENGTH: 26
<212> TYPE: DNA
<213> ORGANISM: Artificial
<220> FEATURE:
<223> OTHER INFORMATION: primer

<400> SEQUENCE: 13
agatctatga ataatttcga cctgca                                       26

<210> SEQ ID NO 14
<211> LENGTH: 31
<212> TYPE: DNA
<213> ORGANISM: Artificial
<220> FEATURE:
<223> OTHER INFORMATION: primer

<400> SEQUENCE: 14
ctcgagaagc ttagcgtgca gcctcgtaaa t                                 31

METHOD OF PRODUCING 1,3-PROPANEDIOL USING RECOMBINANT *KLEBSIELLA* STRAIN IN WHICH GLYCEROL OXIDATIVE PATHWAY HAS BEEN BLOCKED

TECHNICAL FIELD

The present invention relates to a method of producing 1,3-propanediol by culturing a recombinant strain in which the glycerol oxidative pathway had been blocked, and more particularly to a method of producing 1,3-propanediol by two-step culture of a recombinant strain in which the oxidative metabolic pathway that produces byproducts in the glycerol metabolic pathway had been blocked.

BACKGROUND ART 1,3-propanediol can be used as a raw material for synthesizing polyester, polyether or polyurethanes and is used in various applications, including fibers, such as highly functional clothes, carpets or automotive fabrics, and plastic films. In particular, polytrimethylene terephthalate (PTT) that is produced by polymerization of 1,3-propanediol with terephtalic acid has excellent physical properties and a melting point of 228° C. which is lower than that of polyethylene terephthalate (PET). Thus, polytrimethylene terephthalate has high utility and is receiving as a next-generation fiber material capable of substituting for PET. Also, the plastics and polymers produced from 1,3-propanediol as a monomer show excellent optical stability compared to the products produced from butanediol or ethylene glycol. In addition, 1,3-propanediol can be used as a polyglycol-type lubricant and a solvent, and thus its commercial value is evaluated to be higher than that of glycerol.

1,3-propanediol can be produced by chemical synthesis or microbial fermentation. Chemical processes for producing 1,3-propanediol include a process of converting ethylene oxide to 1,3-propanediol by hydroformylation (U.S. Pat. No. 3,687,981) and a process of converting acrolein to 1,3-propanediol by hydration (U.S. Pat. No. 5,015,789). However, such chemical processes have problems in that they require a high-temperature or high-pressure process during the production of 1,3-propanediol, leading to high production costs, and generate waste oil containing environmental pollutants.

Biological processes include a process of producing 1,3-propanediol from glycerol using microorganisms such as *Citrobacter, Clostridium, Enterobacter, Klebsiella, Lactobacillus* or the like, which are facultative anaerobic strains (U.S. Pat. No. 5,254,467).

In a metabolic process of converting glycerol to 1,3-propanediol using the above microorganisms, various kinds of oxidation metabolites are produced in large amounts. Particularly, 2,3-butanediol which is an oxidative metabolite of glycerol has a boiling point similar to 1,3-propanediol, and thus acts as a great hindrance in a process of purifying 1,3-propanediol. Previously, the present inventors attempted to use a metabolic engineering technique to develop microorganisms which produce only 1,3-propanediol in glycerol metabolism without producing byproducts of oxidative metabolism, including 2,3-propanediol, and as a result, the present inventors used a genetic recombinant technique to construct a mutant in which the oxidative metabolic pathway that produces byproducts in the glycerol metabolic pathway had been blocked so that the mutant has only the reductive metabolic pathway that produces 1,3-propanediol (Korean Patent Application No. 10-2008-0122166). However, it was found that the constructed mutant had low production of 1,3-propanediol, although it produced no byproducts in general batch culture.

Accordingly, the present inventors constructed a mutant strain in which the oxidative metabolic pathway that produces byproducts in the glycerol metabolic pathway had been blocked and have made extensive efforts to increase the production of 1,3-propanediol in culture of the mutant.

As a result, the present inventors have found that, when a two-step culture process is carried out which consists of a first-step culture process in which glycerol is not added to medium and a second-step culture process in which glycerol is added to medium, the yield of 1,3-propanediol will increase, thereby completing the present invention.

DISCLOSURE OF INVENTION

Therefore, it is an object of the present invention to provides a recombinant strain in which the oxidative metabolic pathway that produces byproducts in the glycerol metabolic pathway had been blocked and improve a method for culturing the recombinant strain, thereby providing a method for producing 1,3-propanediol with improved productivity.

To achieve the above object, the present invention provides a microbial mutant in which a transcriptional activator-encoding gene or a dihydroxyacetone kinase-encoding gene was deleted or inactivated in a microorganism having the ability to produce 1,3-propanediol using glycerol as a carbon source and a method of producing 1,3-propanediol by culturing the microbial mutant, the method comprising the steps of: (a) culturing the microbial mutant in a glycerol-free medium to grow cells of the microbial strain; (b) adding glycerol to the culture broth in which the microbial cells have been grown, and further culturing the cells to produce 1,3-propanediol; and (c) recovering the produced 1,3-propanediol.

The present invention also provides a microbial mutant which has the ability to produce 1,3-propanediol using glycerol as a carbon source and in which a vector containing a 1,3-propanediol oxidoreductase-encoding gene was introduced into a *Klebsiella pneumoniae* mutant (AK strain) containing deletions of a glycerol dehydrogenase gene (DhaD), a transcriptional activator gene (DhaR), a 1,3-propanediol oxidoreductase gene (DhaT) and a glycerol dehydratase reactivation factor II gene (DhaBA2) or in which the 1,3-propanediol oxidoreductase-encoding gene was inserted into the chromosome of the mutant (AK strain) and a method of producing 1,3-propanediol by culturing the microbial mutant, the method comprising the steps of: (a) culturing the microbial mutant in a glycerol-free medium to grow cells of the microbial strain; (b) adding glycerol to the culture broth in which the microbial cells have been grown, and further culturing the cells to produce 1,3-propanediol; and (c) recovering the produced 1,3-propanediol.

The present invention also provides a microbial mutant which has the ability to produce 1,3-propanediol using glycerol as a carbon source and in which a vector containing a 1,3-propanediol oxidoreductase-encoding gene and a glycerol dehydratase reactivation factor-encoding gene was introduced into a *Klebsiella pneumoniae* mutant (AK strain) containing deletions of a glycerol dehydrogenase gene (DhaD), a transcriptional activator gene (DhaR), a 1,3-propanediol oxidoreductase gene (DhaT) and a glycerol dehydratase reactivation factor II gene (DhaBA2) or in which the 1,3-propanediol oxidoreductase-encoding gene and the glycerol dehydratase reactivation factor-encoding gene were inserted into the chromosome of the mutant (AK strain) and a method of producing 1,3-propanediol by culturing the microbial mutant, the method comprising the steps of: (a) culturing the microbial mutant in a glycerol-free medium to grow cells of the microbial strain; (b) adding glycerol to the culture broth in which the microbial cells have been grown, and further culturing the cells to produce 1,3-propanediol; and (c) recovering the produced 1,3-propanediol.

The present invention also provides a microbial mutant which has the ability to produce 1,3-propanediol using glycerol as a carbon source and in which a vector containing a 1,3-propanediol oxidoreductase-encoding gene was introduced into a *Klebsiella pneumoniae* mutant (AR strain) containing deletions of a transcriptional activator gene (DhaR), a 1,3-propanediol oxidoreductase gene (DhaT) and a glycerol dehydratase reactivation factor II gene (DhaBA2) or in which the 1,3-propanediol oxidoreductase-encoding gene was inserted into the chromosome of the mutant (AR strain) and a method of producing 1,3-propanediol by culturing the microbial mutant, the method comprising the steps of: (a) culturing the microbial mutant in a glycerol-free medium to grow cells of the microbial strain; (b) adding glycerol to the culture broth in which the microbial cells have been grown, and further culturing the cells to produce 1,3-propanediol; and (c) recovering the produced 1,3-propanediol.

The present invention also provides a microbial mutant which has the ability to produce 1,3-propanediol using glycerol as a carbon source and in which a vector containing a 1,3-propanediol oxidoreductase-encoding gene and a glycerol dehydratase reactivation factor—encoding gene was introduced into a *Klebsiella pneumoniae* mutant (AR strain) containing deletions of a transcriptional activator gene (DhaR), a 1,3-propanediol oxidoreductase gene (DhaT) and a glycerol dehydratase reactivation factor II gene (DhaBA2) or in which the 1,3-propanediol oxidoreductase-encoding gene and the glycerol dehydratase reactivation factor-encoding gene were inserted into the chromosome of the mutant (AR strain) and a method of producing 1,3-propanediol by culturing the microbial mutant, the method comprising the steps of: (a) culturing the microbial mutant in a glycerol-free medium to grow cells of the microbial strain; (b) adding glycerol to the medium culture in which the microbial cells have been grown, and further culturing the cells to produce 1,3-propanediol; and (c) recovering the produced 1,3-propanediol.

Other features and embodiments of the present invention will be more apparent from the following detailed descriptions and the appended claims.

BEST MODE FOR CARRYING OUT THE INVENTION

In one aspect, the present invention is directed to a method of producing 1,3-propanediol by culturing a microbial mutant in which a transcriptional activator-encoding gene or a dihydroxyacetone kinase-encoding gene was deleted or inactivated in a microorganism having the ability to produce 1,3-propanediol using glycerol as a carbon source, the method comprising the steps of: (a) culturing the microbial mutant in a glycerol-free medium to grow cells of the microbial strain; (b) adding glycerol to the culture broth in which the microbial cells have been grown, and further culturing the cells to produce 1,3-propanediol; and (c) recovering the produced 1,3-propanediol.

Figure 1:
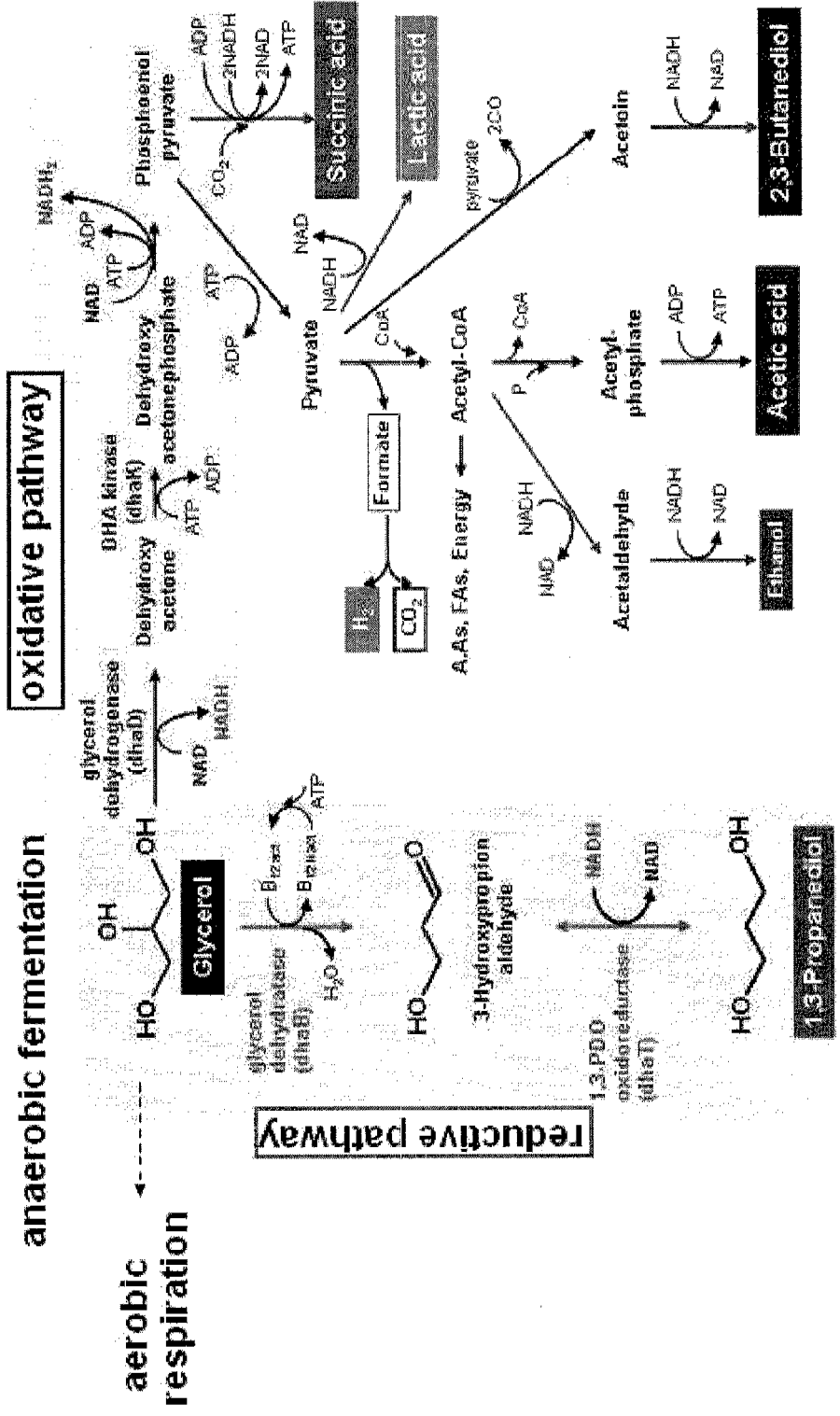
FIG. 1 is a schematic diagram showing a reductive pathway producing 1,3-propanediol and an oxidative pathway producing byproducts in a glycerol metabolic process.

The glycerol metabolic pathway consists of two metabolic pathways: an oxidative metabolic pathway and a reductive metabolic pathway (FIG. 1). In the oxidative metabolic process, glycerol is oxidized to dihydroxyacetone (DHA) by NAD+ dependent glycerol dehydrogenase while producing NADH, which is then converted to dihydroxyacetone phosphate (DHAP) by DHA kinase. The dihydroxyacetone phosphate (DHAP) is metabolized through glycoysis while being used as the carbon and energy sources required for growth. In the oxidative metabolic process, byproducts including 2,3-butanediol, acetic acid, ethanol, lactic acid and succinic acid are produced.

Meanwhile, in the reductive metabolic process, glycerol is converted to 3-hydroxypropionaldehyde by the action of dehyratase, and then reduced to 1,3-propanediol by the action of NADH-dependent oxidoreductase while forming NAD+.

In the present invention, the mutant which is cultured to produce 1,3-propanediol is a microbial strain in which genes encoding proteins involved in the oxidative pathway of the glycerol metabolic process had been deleted or inactivated and which produces only 1,3-propanediol through the reductive pathway without producing byproducts including 2,3-butanediol, ethanol, lactic acid and succinic acid.

The metabolic pathways for glycerol oxidation and reduction are closely connected with each other in order to maintain the NAD+-NADH balance in cells, and the genes encoding the four enzymes, that is, glycerol dehyratase (dhaB), 1,3-propanediol reducatse (dhaT), glycerol dehydrogenase (dhaD) and dihydroxyacetone kinase (dhaK), are arranged in clusters on the chromosome and regulated in the same regulon by the coexisting transcriptional regulator DhaR.

In the present invention, the microorganism having the ability to produce 1,3-propanediol may be a strain selected from the group consisting of *Citrobacter, Clostridium, Enterobacter, Klebsiella* and *Lactobacillus*. Preferably, *Klebsiella pneumoniae* is used in the present invention.

Where the mutant microorganism that is used in the present invention is *Klebsiella pneumoniae*, the transcriptional activator gene is preferably DhaR, and the dihydroxyacetone kinase gene is preferably selected from the group consisting of DhaK, DhaL, DhaM and DhaK'.

In the present invention, the proteins that are involved in the glycerol oxidative pathway of the mutant are preferably glycerol dehydrogenase, transcriptional activator and dihydroxyacetone kinase.

Figure 2:
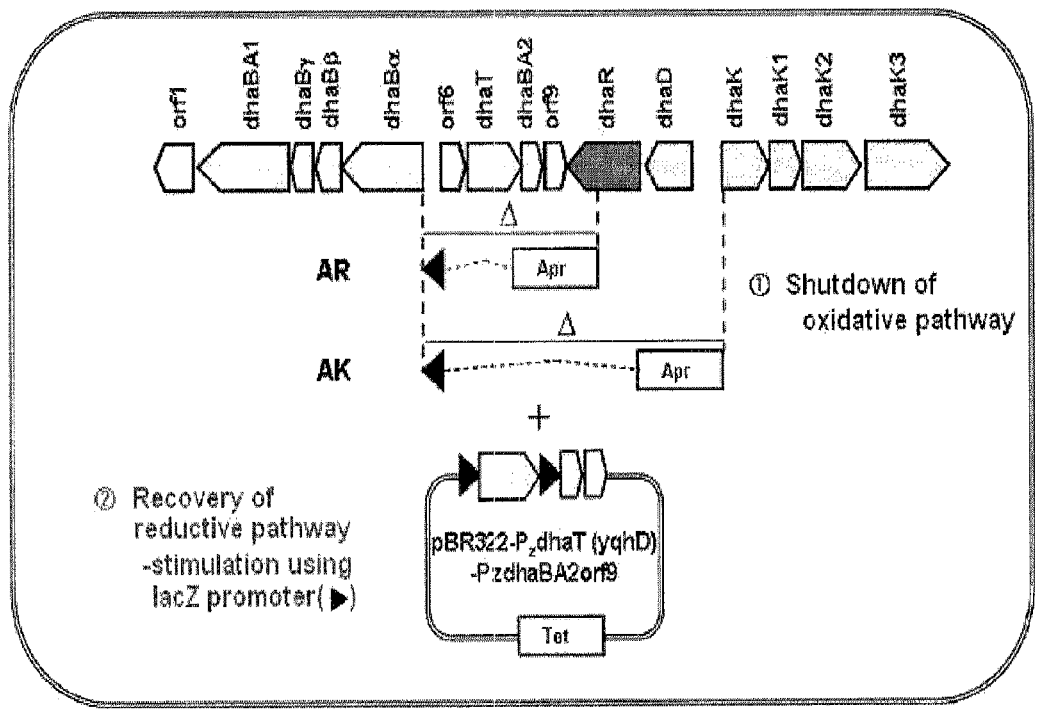
FIG. 2 shows a method for preparing a mutant according to the present invention, shown using the structure of the dha regulon.

A recombinant microorganism which is used in one embodiment of the present invention and in which the glycerol oxidative pathway had been blocked was constructed in the following manner. A *Klebsiella pneumoniae* mutant (AK strain) was constructed by deleting the glycerol dehydrogenase gene (DhaD), the transcriptional activator gene (DhaR), the 1,3-propanediol oxidoreductase gene (DhaT) and the glycerol dehydratase reactivation factor II gene (DhaBA2) from the chromosome of the *Klebsiella pneumoniae* strain. The mutant was transformed with a recombinant vector comprising the 1,3-propanediol oxidoreductase gene (DhaT) and the glycerol dehydratase reactivation factor II gene (DhaBA2), which are genes involved in the glycerol reductive pathway, thus restoring the reductive pathway. As a result, a mutant with deletions of only the 1,3-propanediol oxidoreductase gene (DhaT) and the transcription activator gene (DhaR) was constructed (FIG. 2).

Accordingly, the mutant that is used in one embodiment of the present invention is characterized in that the glycerol dehydrogenase gene (DhaD) and the transcriptional activator gene (DhaR) were deleted or inactivated.

In this process, the lacZ promoter ($P_{lacZ}$) was inserted upstream of the genes involved in the reductive pathway, so that the genes were no longer regulated by the DhaR regulator, whereby the expression of the genes could be artificially controlled using an inducer.

A recombinant microorganism which is used in another embodiment of the present invention and in which the glycerol oxidative pathway had been blocked was constructed in the following manner. A *Klebsiella pneumoniae* mutant (AR strain) was constructed by deleting the transcription activator gene (DhaR), the 1,3-propanediol oxidoreductase gene (DhaT) and the glycerol dehydratase reactivation factor II gene (DhaBA2) from the chromosome of the *Klebsiella pneumoniae* strain. The mutant was transformed with a recombinant vector comprising the 1,3-propanediol oxidoreductase gene (DhaT) and the glycerol dehydratase reactivation factor II gene (DhaBA2), which are genes involved in the reductive pathway of glycerol, thus restoring the reductive pathway. As a result, a mutant with a deletion of only the transcription activator gene (DhaR) was constructed (FIG. 2).

Accordingly, the mutant that is used in another embodiment of the present invention is characterized in that the transcription activator gene (DhaR) was deleted or inactivated.

In another aspect, The present invention is also directed to a method of producing 1,3-propanediol by culturing a microbial mutant which has the ability to produce 1,3-propanediol using glycerol as a carbon source and in which a vector containing a 1,3-propanediol oxidoreductase-encoding gene was introduced into a *Klebsiella pneumoniae* mutant (AK strain) containing deletions of a glycerol dehydrogenase gene (DhaD), a transcriptional activator gene (DhaR), a 1,3-propanediol oxidoreductase gene (DhaT) and a glycerol dehydratase reactivation factor II gene (DhaBA2) or in which the 1,3-propanediol oxidoreductase-encoding gene was inserted into the chromosome of the mutant (AK strain), the method comprising the steps of: (a) culturing the microbial mutant in a glycerol-free medium to grow cells of the microbial strain; (b) adding glycerol to the culture broth in which the microbial cells have been grown, and further culturing the cells to produce 1,3-propanediol; and (c) recovering the produced 1,3-propanediol.

In one embodiment of the present invention, it was found that the *Klebsiella pneumoniae* mutant with deletions of the glycerol dehydrogenase gene (DhaD) and the transcriptional activator gene (DhaR) and the *Klebsiella pneumoniae* mutant with deletions of the transcriptional activator gene (DhaR) produced 1,3-propanediol in a glycerol-containing medium without producing byproducts of the oxidative pathway other than a small amount of acetic acid, but the ability thereof to produce 1,3-propanediol was inferior to that of the wild-type parent strain. To overcome this problem, when the recombinant strains are first cultured in a glycerol-free medium to grow the microbial cells and are then further cultured in a glycerol-containing medium, 1,3-propanediol can be produced in high yield without producing byproducts.

In one embodiment of the present invention, it was found that, when the parent *Klebsiella pneumoniae* Cu strain was cultured in two steps, the glycerol-to-1,3-propanediol conversion rate was 35% (mol/mol), whereas, when the recombinant strain was cultured in two steps, the glycerol-to-1,3-propanediol conversion rate was 70% (mol/mol) which was significantly improved.

In the two-step culture of the present invention, glycerol is preferably added at a concentration of 5-50 g/L, more preferably 5-20 g/L, and most preferably 10 g/L.

Figure 12:
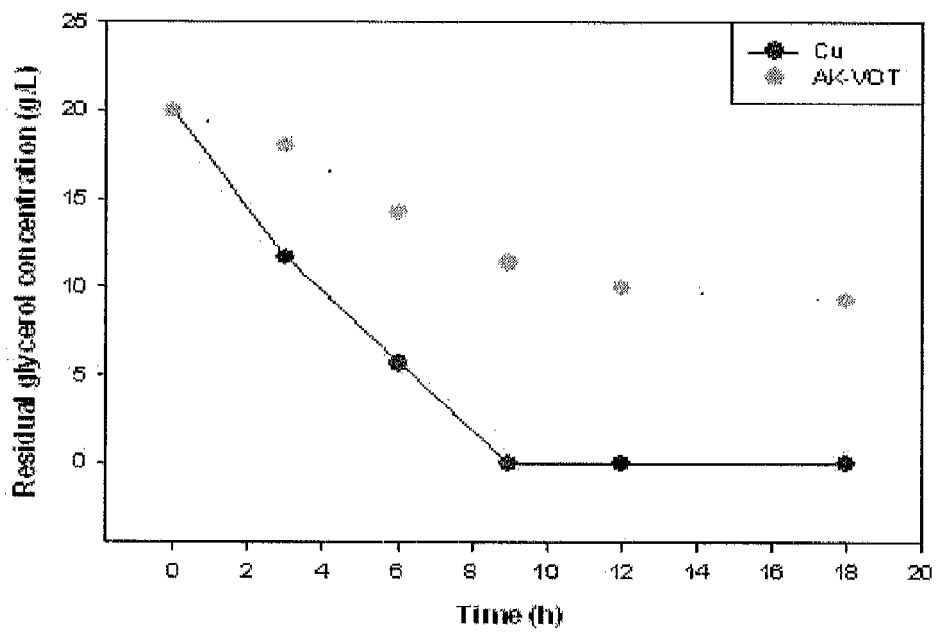
FIG. 12 is a set of graphs showing the concentration of residual glycerol and the concentration of produced 1,3-propanediol in the culture broth obtained after the second-step culture of the recombinant strain used in the present invention.
Figure 12:
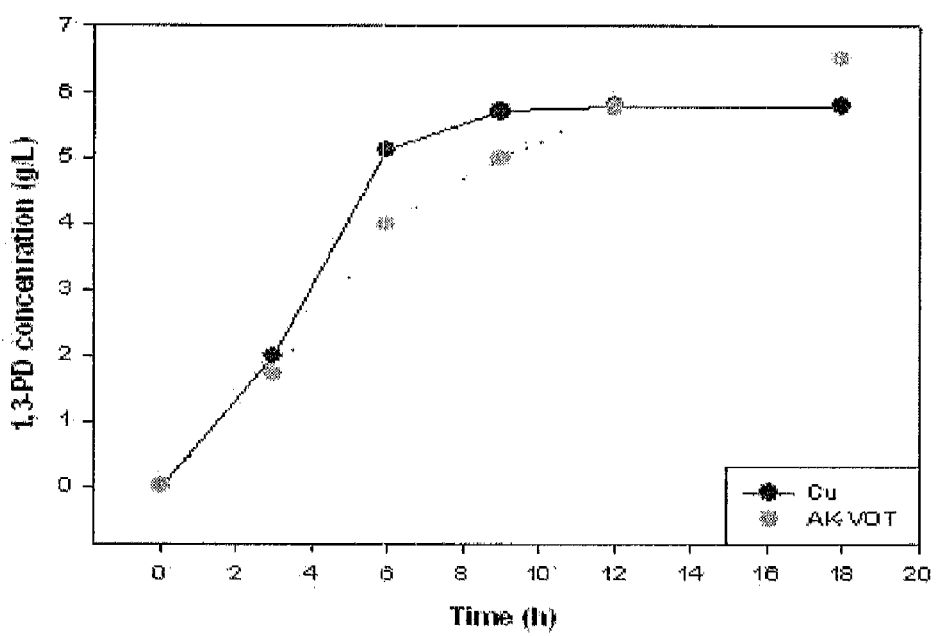

In one embodiment of the present invention, it was found that, at an aeration rate of 0 vvm, little or no glycerol was consumed, and the consumption rate of glycerol and the production of 1,3-propanediol were similar between aeration rates of 0.2 vvm, 0.5 vvm and 1.0 vvm. In another embodiment of the present invention, it was found that, when the pH of the culture medium was maintained at each of 5, 6, 7 and 8 up to the end of the culture period, the production of 1,3-propandiol was the highest at a pH of 6. Also, when the $OD_{600}$ value indicating the degree of growth of the strain reached each of 0, 0.5, 1, 2 and 3, glycerol was added to a final concentration of 20 g/L. In this case, as shown in FIG. 12, the higher the $OD_{600}$ value, the higher was the production of 1,3-propanediol.

To prepare the mutant used in one embodiment of the present invention, the DhaB enzyme reactivation factor, DhaT gene, DhaR regulator and DhaD gene of the dha regulon were substituted with the apramycin-resistant gene by a homologous recombination method using a plasmid DNA-cured *Klebsiella pneumoniae* MGH78578 strain (hereinafter referred to as "Cu") as a parent strain, thereby preparing a recombinant strain with deletions of both the glycerol oxidative and reductive pathways (hereinafter referred to as an "AK" strain). In order to restore the glycerol reductive pathway of the AK strain, a plasmid DNA for restoring the glycerol reductive pathway was prepared. The plasmid DNA was prepared by amplifying a DhaB reactivation enzyme gene (orfW)-orfX DNA fragment and the 1,3-propanediol oxidoreductase activity gene dhaT or yqhD (derived from *E. coli*) or the yqhD homologous gene (derived from *Klebsiella pneumoniae*) and inserting the amplified products downstream of the lacZ promoter of a pGEM TEasy vector. The AK strain was transformed with the plasmid DNA for restoring the glycerol reductive pathway, thereby a recombinant strain for producing 1,3-propanediol.

In one embodiment of the present invention, it was found that the *Klebsiella pneumoniae* strain with deletions of the glycerol dehydrogenase gene (DhaD) and the transcriptional activator gene (DhaR), and the *Klebsiella pneumoniae* strain with a deletion of the transcriptional activator gene (DhaR) produced 1,3-propanediol in a glycerol-containing medium without products of the oxidative pathway other than a small amount of acetic acid.

To prepare the mutant used in one embodiment of the present invention, the DhaB enzyme reactivation factor, DhaT gene and DhaR regulator of the dha regulon were substituted with the apramycin-resistant gene by a homologous recombination method using a plasmid DNA-cured *Klebsiella pneumoniae* MGH78578 strain (hereinafter referred to as "Cu") as a parent strain, thereby preparing a recombinant strain with deletions of both the glycerol oxidative and reductive pathways (hereinafter referred to as an "AR" strain). In order to restore the glycerol reductive pathway of the AR strain, the AR strain was transformed with the plasmid DNA for restoring the glycerol reductive pathway, prepared in one embodiment of the present invention, thereby a recombinant strain having the ability to produce 1,3-propanediol without producing byproducts.

Recovery of 1,3-propanediol from the culture broth of the mutant can be carried out using conventional isolation techniques, for example, distillation, electrodialysis, evaporation, chromatography, solvent extraction, and reaction extraction, and these techniques may generally be used in combination to isolate highly pure substances.

As used herein, the term "deletion" of genes refers to the state in which the genes were deleted from a chromosome or a plasmid, so that proteins encoded by the genes could not be produced. The term "inactivation" of genes refers to the state in which the genes were inserted, translocated or partially deleted, such that proteins encoded by the genes could not be produced.

Insertion of the genes into the chromosome of a host cell can be carried out: using a conventional gene manipulation method known in the art. For example, insertion of the genes can be carried out using a retroviral vector, an adenoviral vector, an adeno-associated viral vector, a herpes simplex viral vector, a poxvirus vector, a lentiviral vector or a non-viral vector.

EXAMPLES

Hereinafter, the present invention will be described in further detail with reference to examples. It will be obvious to a person having ordinary skill in the art that these examples are illustrative purposes only and are not to be construed to limit the scope of the present invention.

In the following examples, a mutant in which both the glycerol oxidative and reductive pathways of the *Klebsiella pneumoniae* strain had been blocked was prepared, and the glycerol reductive pathway was restored again, thus preparing a mutant having the ability to produce 1,3-propanediol without producing byproducts. However, it will be obvious to those skilled in the art that a mutant having the ability to produce 1,3-propanediol without producing byproducts can be prepared by blocking only the glycerol oxidative pathway of a microorganism having the ability to produce 1,3-propanediol from glycerol, and culture of this mutant will provide the same results.

Also, in the following examples, a strain transformed with a vector containing genes involved in the glycerol reductive pathway was used to restore the glycerol reductive pathway of the mutant in which both the glycerol oxidative and reductive pathways had been blocked. However, it will be obvious to those skilled in the art that the use of a strain obtained by inserting the glycerol reductive pathway genes into the chromosome of the mutant using a conventional insertion method can also provide the same results.

Example 1

Preparation of Recombinant Strains in which Glycerol Oxidative-Reductive Metabolic Pathways Had been Blocked For a redesign of the glycerol metabolic pathway, recombinant strains (AK and AR) in which the glycerol metabolic pathway in *Klebsiella pneumoniae* MGH 78578 (ATCC 700721) had been completely blocked were prepared.

Using a plasmid DNA-cured *Klebsiella pneumoniae* MGH 78578 strain (named "Cu") as a parent strain, the DhaB enzyme reactivation factor, DhaT gene, DhaR regulator and DhaD gene of the dha regulon (FIG. 2) were substituted with apramycin-resistant genes by a homologous recombination method, thereby preparing a recombinant strain AK with deletions of both the glycerol oxidative and reductive pathways. Meanwhile, a recombinant strain AR was prepared by substituting the DhaB enzyme reactivation factor, the DhaT gene and the DhaR regulator with the apramycin-resistant gene. Herein, the DhaR-dependent promoter upstream of the DhaB gene was replaced with an artificially controllable lacZ promoter.

*Klebsiella pneumoniae* MGH 78578 was cultured several times in an antibiotic-free liquid medium, after which colonies were selected from the culture broth and inoculated into a medium containing or not containing tetracycline. A colony that did not grow in the tetracycline-containing medium due to the loss of the plasmid DNA was selected from the colonies and was named "*Klebsiella pneumoniae* MGH 78578 Cu". The selected colony was used as a parent strain for preparing recombinant strains.

DNA fragments for preparing a plasmid for homologous recombination were amplified by PCR using the chromosomal DNA of the *Klebsiella pneumoniae* MGH78578 strain as a template and the following primer sets (FIG. 2):

Primers for amplification of a dhaBI gene fragment

```
SEQ ID NO: 1:
5'-TCTAGAATGAAAAGATCAAAACGATTT-3'
(dhaBI XbaI-480bpF)

SEQ ID NO: 2:
5'-GGATCCGTCAGCGGCAATCTGCAC-3'
(dhaBI BamHI-480 bpR)
```

Primers for amplification of a dhaK gene fragment

```
SEQ ID NO: 3:
5'-AAGCTTCATGCTCTCCGGCGCCTGTC-3'
(dhaK HindIII-200-700 bpF)

SEQ ID NO: 4:
5'-AGATCTATTTGGTCCAGCGAGCTGAAGC-3'
(dhaK BglII-200-700bpR)
```

Primers for amplification of a dhaR gene fragment

```
SEQ ID NO: 5:
5'-AGATCTCCTGGGATTTCGCGACGGCA-3'
(dhaR bglII-200-700bpF)

SEQ ID NO: 6:
5'-AAGCTTTCGACAATCGGTTTTAAGGTG-3'
(dhaR HindIII-200-700bpR)
```

Primers for amplification of an Apr gene fragment

```
SEQ ID NO: 7:
5'-GTTAACCTGACGCCGTTGGATACACC-3'
Apr HpaI F

SEQ ID NO: 8:
5'-AGATCTAAAAGCTTATGAGCTCAGCCAATCGA-3'
Apr HindIII-BglIIR
```

The amplified DNA fragments were cloned into a pGEM TEasy vector and sequenced. Then, as shown in FIGS. 3 and 4, plasmid DNAs were constructed using the vector.

Figure 3:
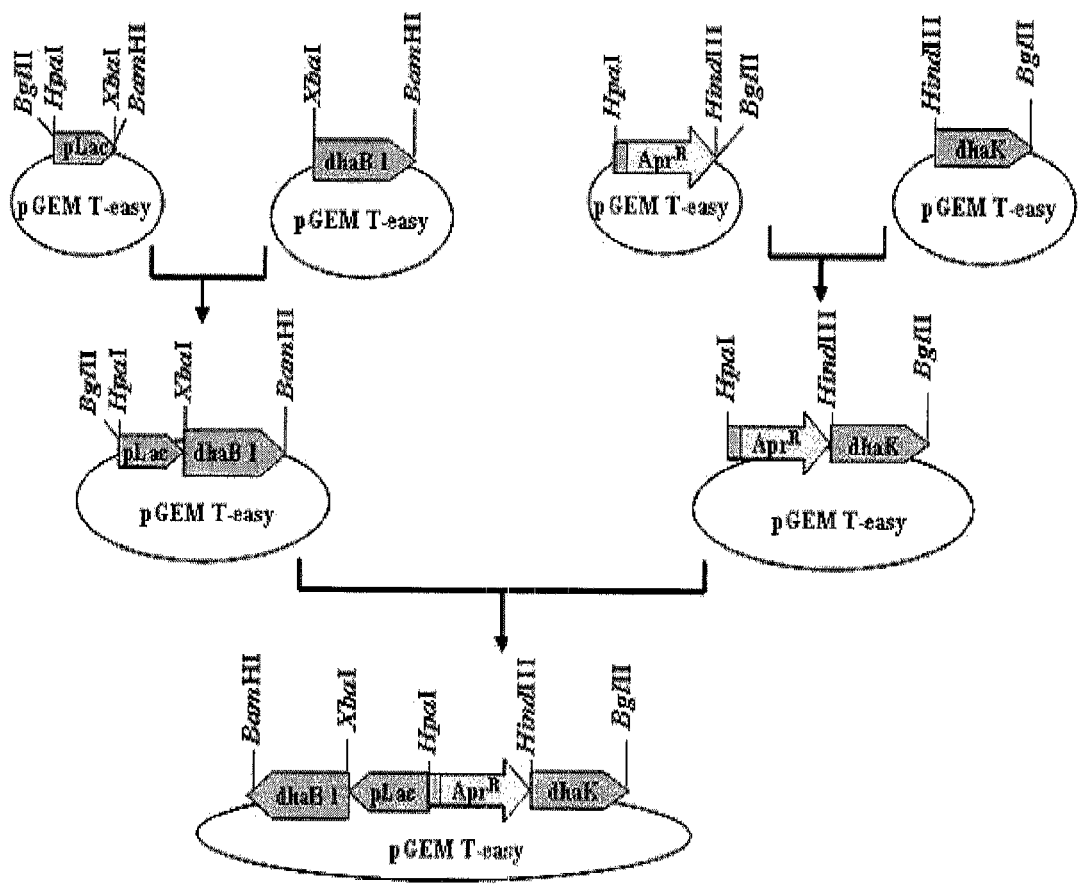
FIG. 3 shows a method for constructing a plasmid DNA, in which the plasmid DNA is used to prepare an AK strain according to the present invention and comprises a linkage of DhaB gene amino terminus (dhaB')-LacZ promoter ($P_{lacZ}$)-Apramycin resistant gene-DhaK gene amino terminus (dhaK').
Figure 4:
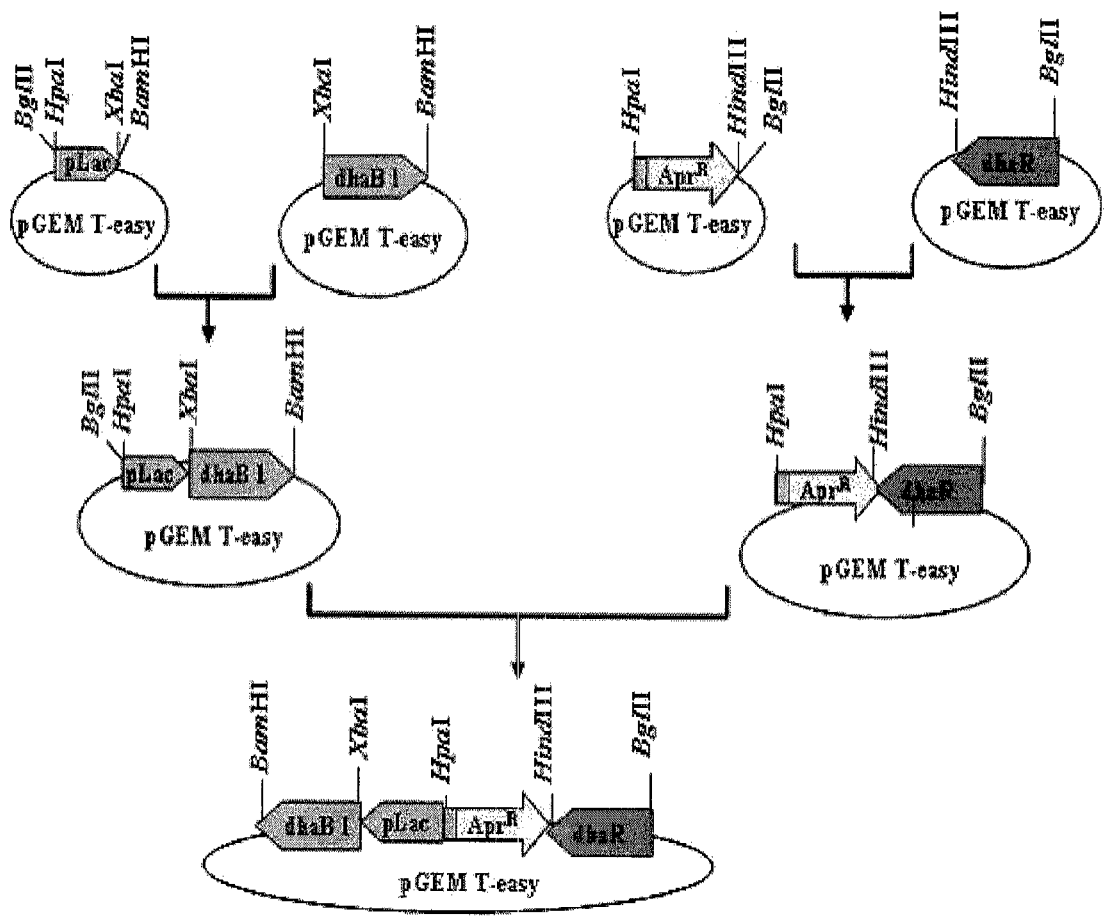
FIG. 4 shows a method for constructing a plasmid DNA, in which the plasmid DNA is used to prepare an AR strain according to the present invention and comprises a linkage of DhaB gene amino terminus (dhaB')-LacZ promoter ($P_{lacZ}$)-Apramycin resistant gene-DhaR gene amino terminus (dhaR').

In the method shown in FIG. 3, the plasmid DNA for preparing the AK strain comprising a linkage of DhaB gene amino terminus (dhaB')-LacZ promoter $P_{lacZ}$-apramycin resistant gene-DhaK gene amino terminus (dhaK') was constructed. In the method shown in FIG. 4, the plasmid DNA for preparing the AR strain comprising a linkage of DhaB gene amino terminus (dhaB')-LacZ promoter $P_{lacZ}$-apramycin resistant gene-DhaR gene amino end (dhaR') was constructed.

Each of the plasmids was treated with BamHI-BglII, and the collected DNA fragment was introduced into the *Klebsiella pneumoniae* Cu strain by electroporation. Then, recombinant strains forming colonies in a medium supplemented with apramycin were isolated from the Cu strain cells. As a result, a recombinant strain AK with deletions of the DhaB enzyme reactivation factor, DhaT gene, DhaR regulator and DhaD gene of the dha regulon and insertions of the lacZ promoter and the apramycin resistant gene was obtained, and a recombinant strain AR with deletions of the DhaB enzyme reactivation factor, the DhaT gene and the DhaR regulator and insertions of the lacZ promoter and the apramycin resistant gene was obtained.

Example 2

Figure 5:
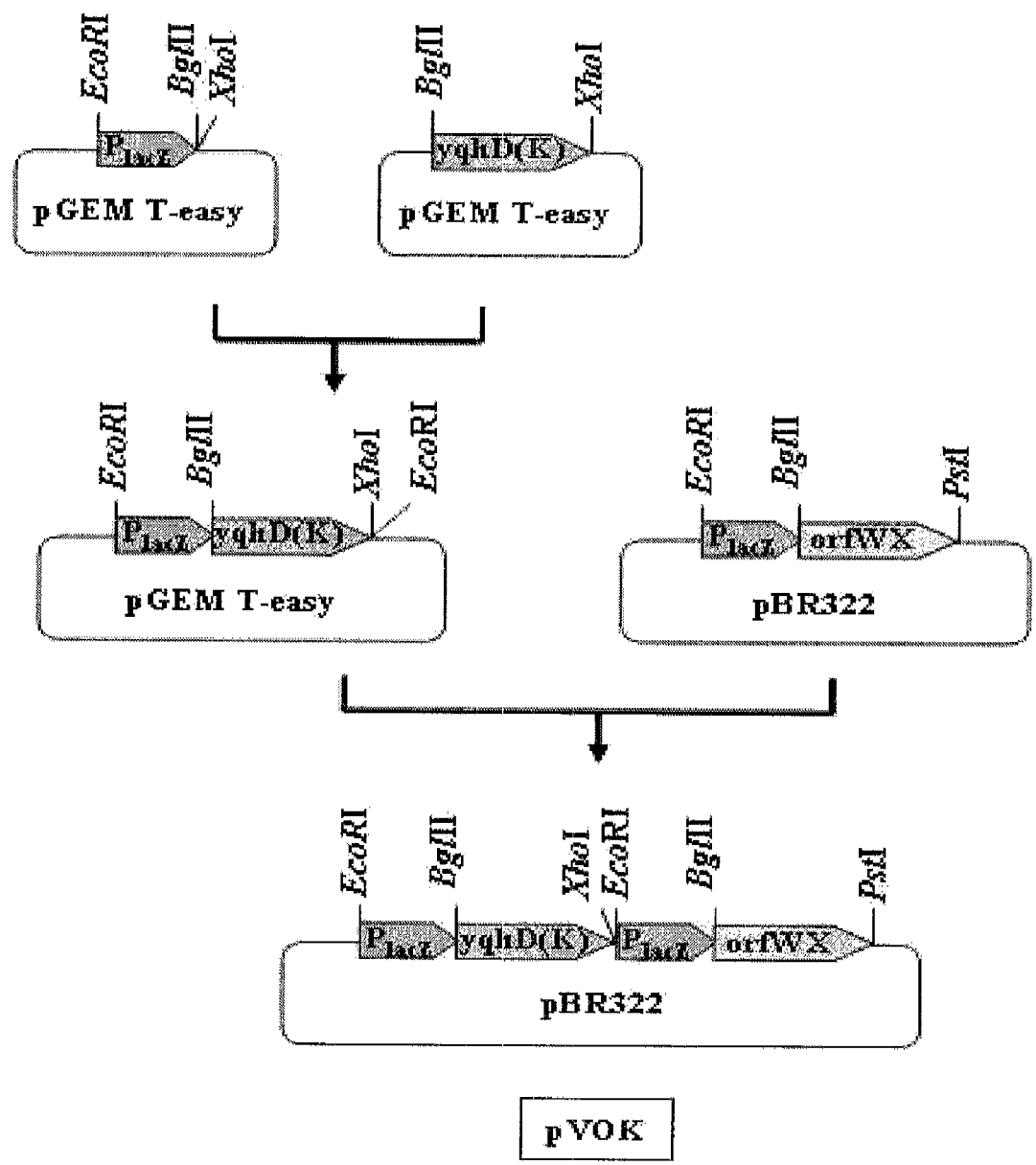
FIG. 5 shows a method for constructing a plasmid DNA comprising the DhaT gene and DhaB reactivation enzyme gene of *Klebsiella pneumoniae* downstream of the lacZ promoter.

Preparation of Strains in which Glycerol Reductive Pathway Had been Restored (1) Preparation of Plasmid DNA for Restoring Glycerol Reductive Pathway A DhaB reactivation enzyme gene (orfW)-orfX DNA fragment and the 1,3-propanediol oxidoreductase activity gene dhaT or yqhD (derived from *E. coli*) or yqhD homologous gene (derived from *Klebsiella pneumoniae*) were amplified using the primer sequences shown below. The amplified genes were cloned into a pGEM TEasy vector and sequenced. Then, as shown in FIG. 5, a plasmid DNA was prepared using the vector.

```
SEQ ID NO: 9:
5'-AGATCTATGAGCTATCGTATGTTTGA-3'
(dhaT-BglII F)

SEQ ID NO: 10:
5'-CTCGAGAAGCTTCAGAATGCCTGGCGGAAAAT-3'
(dhaT-HindIII/XhoI R)

SEQ ID NO: 11:
5'-AGATCTATGAACAACTTTAATCTGCAC-3'
(yqhD-BglII F)

SEQ ID NO: 12:
5'-AGATCTATGAATAATTTCGACCTGCA-3'
(yqhD-HindIII/XhoI R)

SEQ ID NO: 13:
5'-AGATCTATGAATAATTTCGACCTGCA-3'
(yqhD Kle BglII F)

SEQ ID NO: 14:
5'-CTCGAGAAGCTTAGCGTGCAGCCTCGTAAAT-3'
(yqhD Kle HindIII, XhoI R)
```

Figure 6:
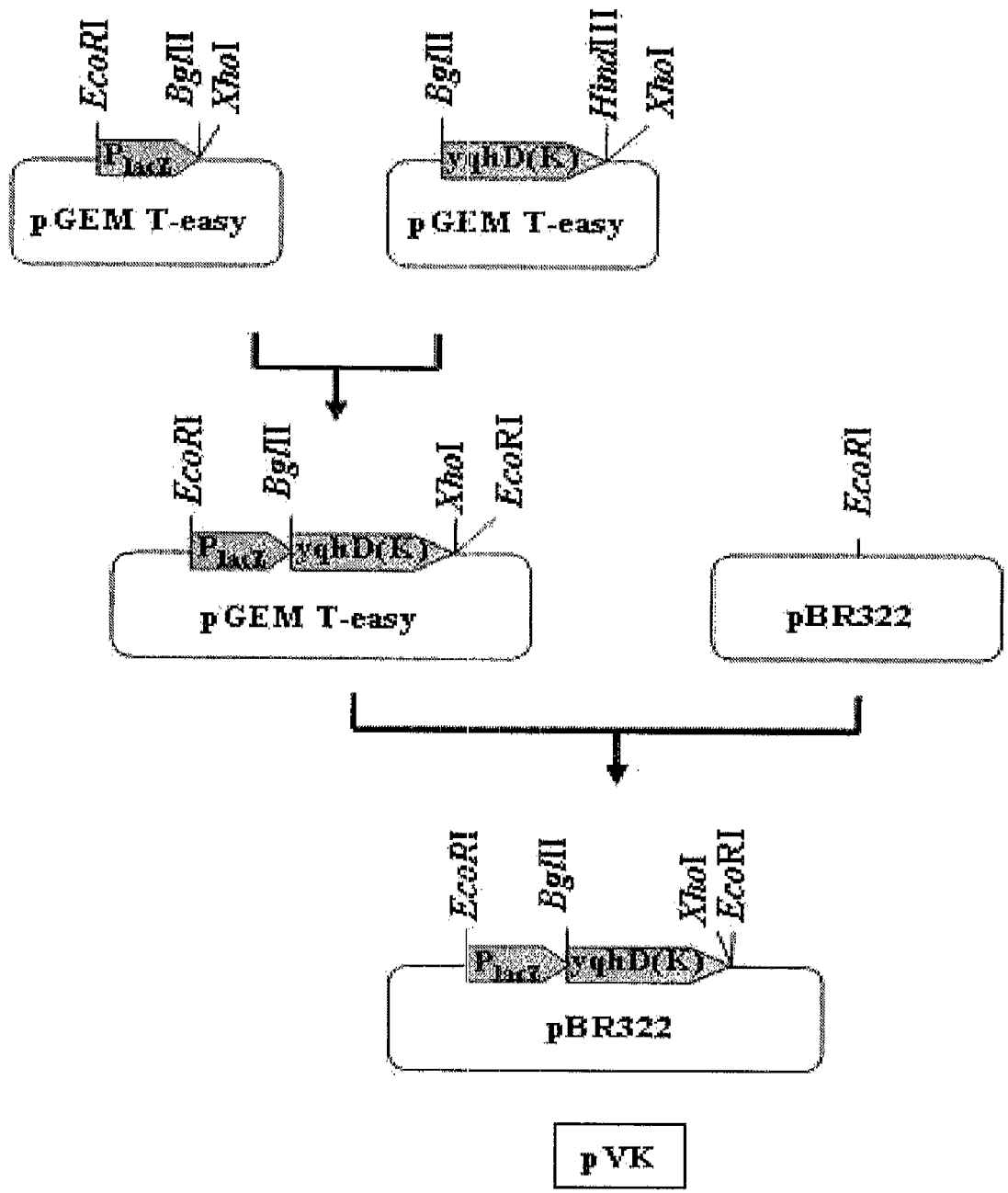
FIG. 6 shows a method for constructing a plasmid DNA comprising only the DhaT gene of *Klebsiella pneumoniae* downstream of the lacZ promoter.
Figure 7:
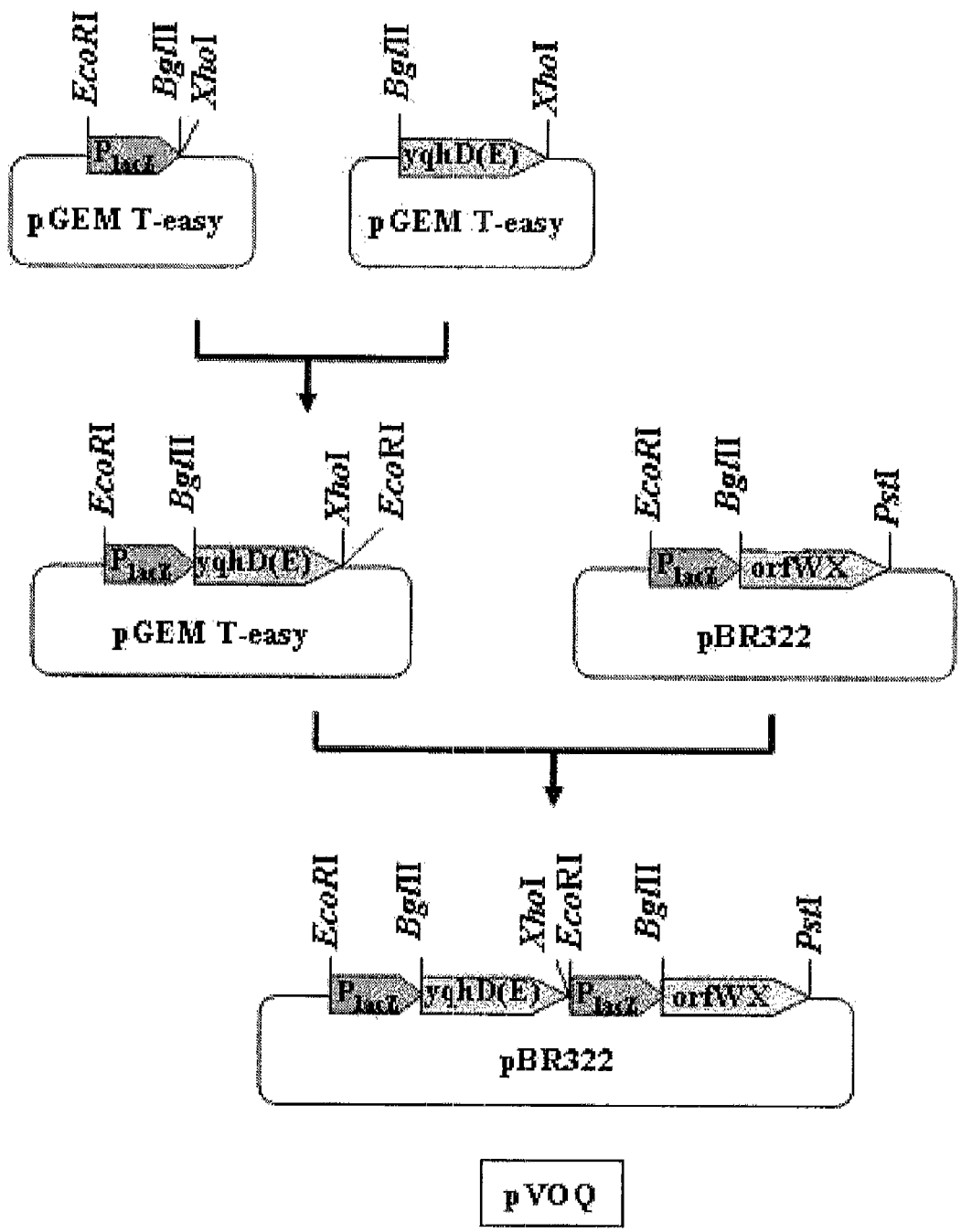
FIG. 7 shows a method for constructing a plasmid DNA comprising the 1,3-propanediol oxidoreductase activity YqhD(E) gene (derived from *E. coli*) and the DhaB reactivation enzyme gene downstream of the lacZ promoter.
Figure 8:
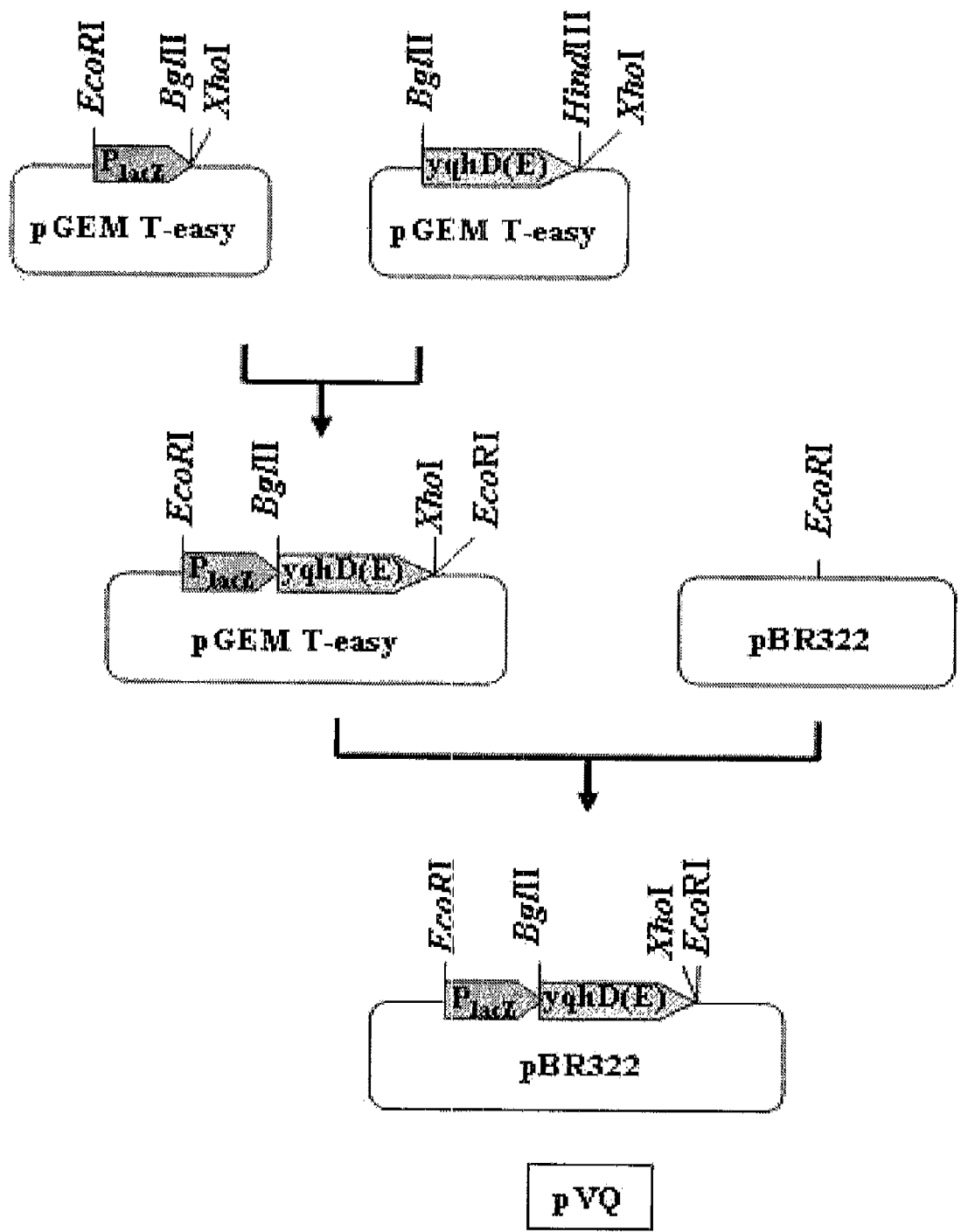
FIG. 8 shows a method for constructing a plasmid DNA comprising only the 1,3-propanediol oxidoreductase activity YqhD(E) gene (derived from *E. coli*) downstream of the lacZ promoter.
Figure 9:
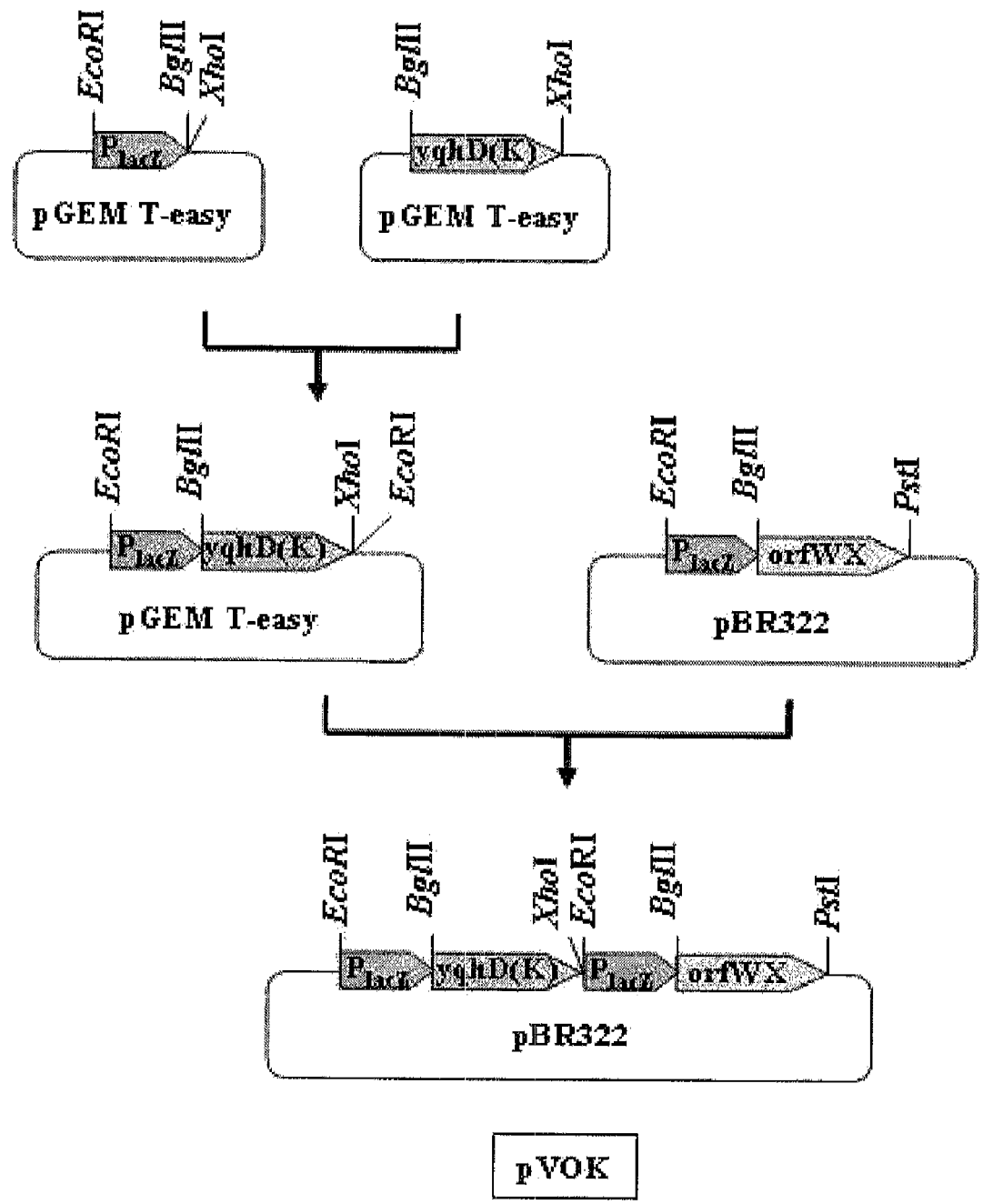
FIG. 9 shows a method for constructing a plasmid DNA comprising the 1,3-propanediol oxidoreductase activity YqhD(K) gene (derived from *K. pneumoniae*) and the DhaB reactivation enzyme gene downstream of the lacZ promoter.
Figure 10:
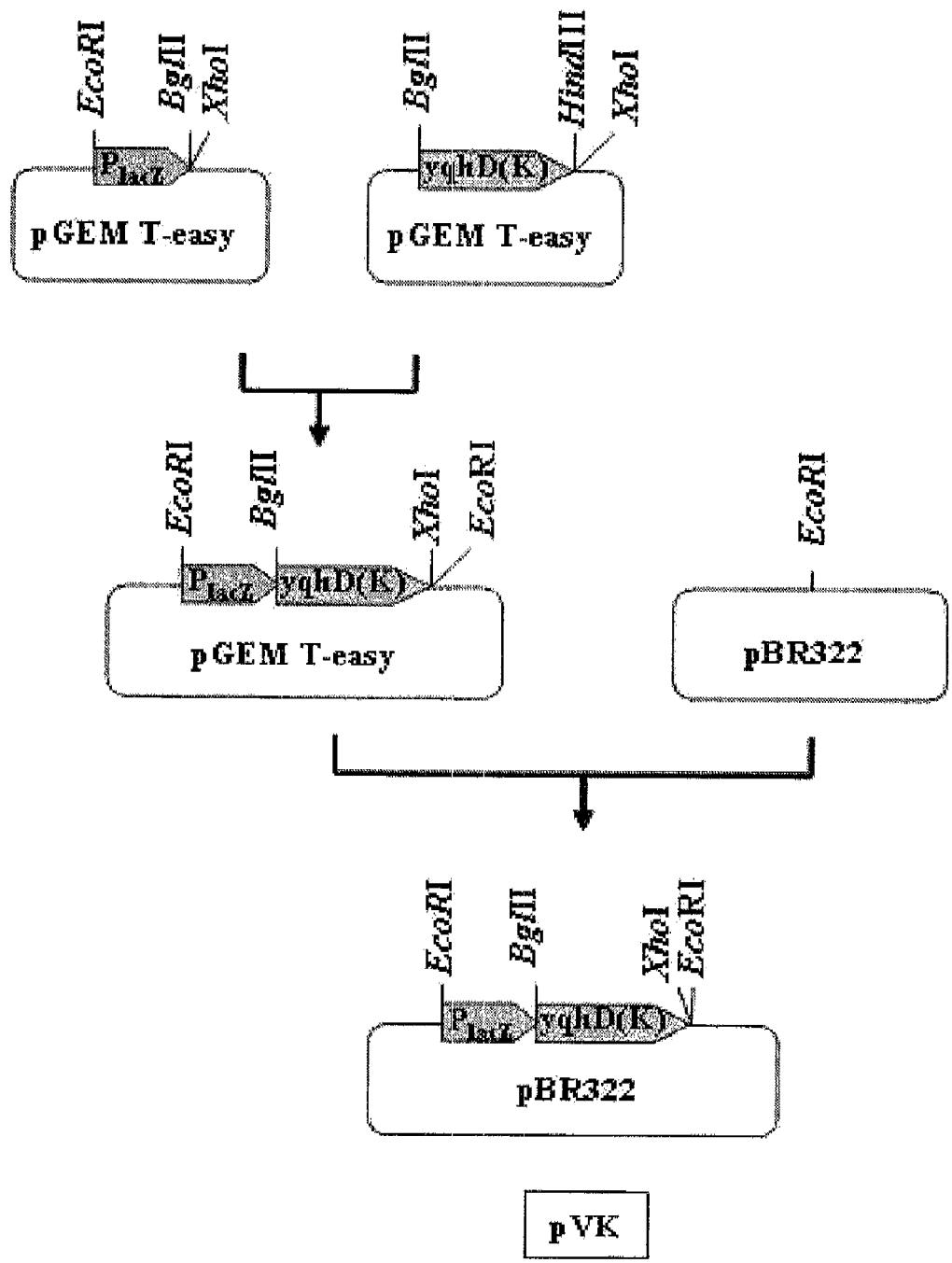
FIG. 10 shows a method for constructing a plasmid DNA comprising only the 1,3-propanediol oxidoreductase activity YqhD(K) gene (derived from *K. pneumoniae*) downstream of the lacZ promoter.

FIGS. 5 and 6 show a process either for constructing a plasmid DNA containing the DhaT gene and DhaB reactivation enzyme gene of *Klebsiella pneumoniae* downstream of the lacZ promoter or for constructing a plasmid DNA containing only the DhaT gene downstream of the lacZ promoter, and FIGS. 7 and 8 show a process either for constructing a plasmid DNA containing the 1,3-propanediol oxidoreductase activity YqhD(E) gene (derived from *E. coli*) and the DhaB reactivation enzyme gene downstream of the lacZ promoter or for constructing a plasmid DNA containing only the YqhD (E) gene downstream of the lacZ promoter. FIGS. 9 and 10 show a process either for constructing a plasmid DNA containing the 1,3-propanediol oxidoreductase activity YqhD(K) gene (derived from *Klebsiella pneumoniae*) and the DhaB reactivation enzyme gene downstream of the lacZ promoter or for constructing a plasmid DNA containing only the YqhD (K) gene downstream of the lacZ promoter.

(2) Preparation of Recombinant Strains in which Reductive Pathway of Glycerol Had been Restored Each of the above-constructed six kinds of plasmid DNAs containing the gene encoding 1,3-propanediol oxidoreductase activity enzyme, and control plasmid DNAs containing pBR322 and the DhaB reactivation enzyme gene was introduced by electroporation into each of the AK and AR strains in which the anaerobic metabolic pathway of glycerol had been blocked, thereby preparing recombinant strains in which the glycerol reductive pathway had been restored (Table 1). The recombinant strain in which each of the plasmids had been introduced into the parent strain Cu was used as a control. The recombinant strains constructed in this Example were deposited in compliance with the Budapest Treaty at the Biological Resource Center in the Korea Research Institute of Bioscience and Biotechnology (Table 2) located at 111 Gwahangno, Yuseong-gu, Daejeon 305-806, Republic of Korea. The listed deposits will be maintained for at least thirty (30) years and will be irrevocably and without restriction released to the public upon the grant of a patent. The availability of a deposit does not constitute a license to practice the subject invention in derogation of patent rights granted by government action.

TABLE 1

Recombinant strains and plasmid DNAs used or constructed in the present invention Significant Genotype Strains

| | |
|---|---|
| E. coli DH5a | Cloning Host |
| K. pneumoniae Cu | Tet$^R$contained Plasmid DNA curing K. pneumoniae MGH 78578 |
| K. pneumoniae AK | (orfY-dhaT-orfW-orfX-dhaR-dhaD)::P$_{LacZ}$-Apr$^R$ |
| K. pneumoniae AR | (orfY-dhaT-orfW-orfX-dhaR)::P$_{LacZ}$-Apr$^R$ |

Plasmids

| | |
|---|---|
| pV | pBR322 |
| pVO | pBR322-P$_{LacZ}$orfW-orfX |
| pVOT | pBR322-P$_{LacZ}$orfW-orfX-P$_{LacZ}$dhaT |
| pVT | pBR322-P$_{LacZ}$dhaT |
| pVOQ | pBR322-P$_{LacZ}$orfW-orfX-P$_{LacZ}$yqhD (E. coli) |
| pVQ | pBR322-P$_{LacZ}$yqhD (E. coli) |
| pVOK | pBR322-P$_{LacZ}$orfW-orfX-P$_{LacZ}$yqhD (K. pneumoniae) |
| pVK | pBR322-P$_{LacZ}$yqhD (K. pneumoniae) |

TABLE 2

Deposit numbers of recombinant strains according to the present invention

| Strains | Deposit No. | Deposit Date |
|---|---|---|
| Klebsiella pneumoniae AK | KCTC11419BP | 12 Nov. 2008 |
| Klebsiella pneumoniae AR | KCTC11420BP | 12 Nov. 2008 |
| Klebsiella pneumoniae AK-VOT | KCTC11421BP | 12 Nov. 2008 |
| Klebsiella pneumoniae AK-VOK | KCTC11422BP | 12 Nov. 2008 |
| Klebsiella pneumoniae AR-VOT | KCTC11423BP | 12 Nov. 2008 |
| Klebsiella pneumoniae AR-VOK | KCTC11424BP | 12 Nov. 2008 |

Example 3

Production of 1,3-Propanediol by Fermentation of Klebsiella pneumoniae Cu, AK-VOT, AK-VOQ and AK-VOK Each of the Klebsiella pneumoniae Cu, AK-VOT, AK-VOQ and AK-VOK strains was cultured in a 5-L fermentor, and the degree of growth of each strain was examined. In addition, the concentration of residual glycerol and the production of metabolic products including 1,3-propanediol were analyzed by chromatography. The medium used in the culture process had the following composition: 20 g/l glycerol, 3.4 g/l K$_2$HPO$_4$, 1.3 g/l KH$_2$PO$_4$, 0.2 g/l MgSO$_4$, 0.002 g/l CaCl$_2$2H$_2$O, 1 g/l yeast extract, 1 ml iron solution [5 g/l FeSO$_4$7H$_2$O, 4 ml HCl (37%, w/v)] and 1 ml trace element solution [70 mg/l ZnCl$_2$, 100 mg/l MnCl$_2$4H$_2$O, 60 mg/l H$_3$C$_3$, 200 mg/l CoCl$_2$4H$_2$O, 20 mg/l CuCl$_2$2H$_2$O, 25 mg/l NiCl$_2$6H$_2$O, 35 mg/l Na$_2$MoO$_4$2H$_2$O, 4 ml HCl (37%, w/v)].

The culture process was carried out under the following conditions: the effective volume of the 5-L fermentor: 2 L, the final concentration of IPTG: 0.5 mM, the final concentration of tetracycline: 10 µg/L, inoculation concentration: 1%, culture temperature: 37° C., stirring rate: 200 rpm, and aeration rate: 0.5 vvm.

Figure 11:
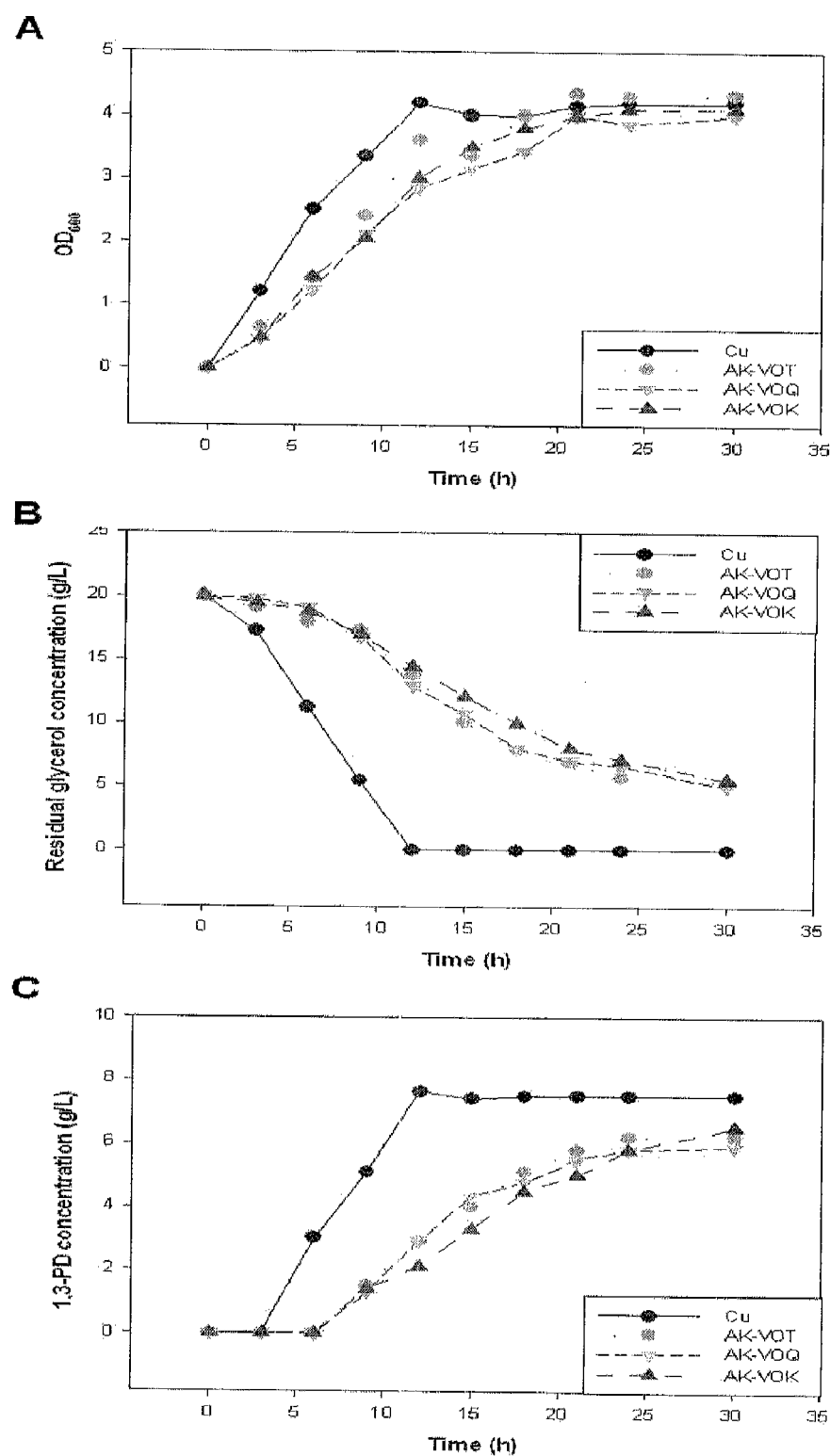
FIG. 11 is a set of graphs showing the components of the culture broth obtained after the one-step culture of the recombinant strain used in the present invention.

As a result, as shown in FIG. 11, the control Cu strain showed a higher growth rate than the other strains, but the final OD$_{600}$ value was about 4 and similar between all the strains. With respect to the remaining glycerol, the Cu strain completely consumed 2% glycerol at 12 hours of culture and produced 7.63 g/L of 1,3-propanediol together with other oxidative metabolic products, including 2,3-butanediol (2.35 g/L), ethanol (1 g/L), lactic acid (1 g/L), acetic acid (0.4 g/L) and succinic acid (0.3 g/L). On the other hand, the AK-VOT, AK-VOQ and AK-VOK strains showed a residual glycerol concentration of 5 g/L or more even after 30 hours of culture and produced 6 g/L of 1,3-propanediol, but produced no byproducts, unlike the Cu strain. The 1,3-propanediol productivity was higher by more than 1 g/L in the Cu strain than in the AK-VOT, AK-VOQ and AK-VOK strains, but the glycerol-to-1,3-propanediol conversion rate was lower by about 10% in the Cu strain than in the other strains.

TABLE 3

Results of one-step fermentation of the AK/pVOT strain prepared in the present invention

| Strain (Culture time) | Cu/pV (12 hr) | AK/pVOT (24 hr) |
|---|---|---|
| Residual glycerol (g/L) | 0 | 5.7 |
| 1,3-PD production (g/L) | 7.63 | 6.18 |
| 2,3-butanediol (g/L) | 2.35 | 0 |
| ethanol (g/L) | 1.0 | 0 |
| Lactic acid (g/L) | 1.0 | 0 |
| Succinic acid (g/L) | 0.3 | 0 |
| Acetic acid (g/L) | 0.4 | 1 |
| Glycerol-to-1,3-PD conversion rate (%, mol/mol) | 44 | 52 |
| 1,3-PD productivity (g/Lh) | 0.61 | 0.26 |

Example 4

Production of 1,3-Propanediol by Two-Step Fermentation

In order to improve the low 1,3-propanediol productivity of the AK-VOT strain, the two-step fermentation of the strain was carried out under the following conditions: the effective volume of the 5-L fermentor: 2 L, the final concentration of IPTG: 0.5 mM, the final concentration of tetracycline: 10 µg/L, the inoculation concentration of the strain: 1%, culture temperature: 37° C., stirring rate: 200 rpm, and aeration rate: 0.5 vvm. The strain that has been pre-cultured in LB medium was inoculated into 2 L of LB medium at a concentration of 1%, followed by first-step fermentation (strain culture step). 12 hours after the start of the first-step fermentation, glycerol was added to the culture broth at a concentration of 20 g/L, followed by second-step fermentation (1,3-propanediol producing step), thereby inducing the metabolism of glycerol. As a result, in comparison with the one-step fermentation carried out in Example 3 above, the glycerol-to-1,3-propanediol conversion rate was increased from 52% to 70%, and the 1,3-propoanediol productivity of the strain was improved from 0.26 g/Lh to 0.56 g/Lh (increased more than two times) (Table 12 and Table 4).

TABLE 4

Results of two-step fermentation of AK-VOT strain

| Strain (Culture time) | Cu/pV (9 hr) | AK/pVOT (9 hr) |
|---|---|---|
| Residual glycerol (g/L) | 0 | 11.4 |
| 1,3-PD production (g/L) | 5.8 | 5 |
| 2,3-butanediol (g/L) | 2.35 | 0 |
| ethanol (g/L) | 1.0 | 0 |
| Lactic acid (g/L) | 1.0 | 0 |
| Succinic acid (g/L) | 0.3 | 0 |
| Acetic acid (g/L) | 0.4 | 0.5 |
| Glycerol-to-1,3-PD conversion rate (%, mol/mol) | 35 | 70 |
| 1,3-PD productivity (g/Lh) | 0.64 | 0.56 |

Example 5

Effect of Glycerol Concentration

Figure 13:
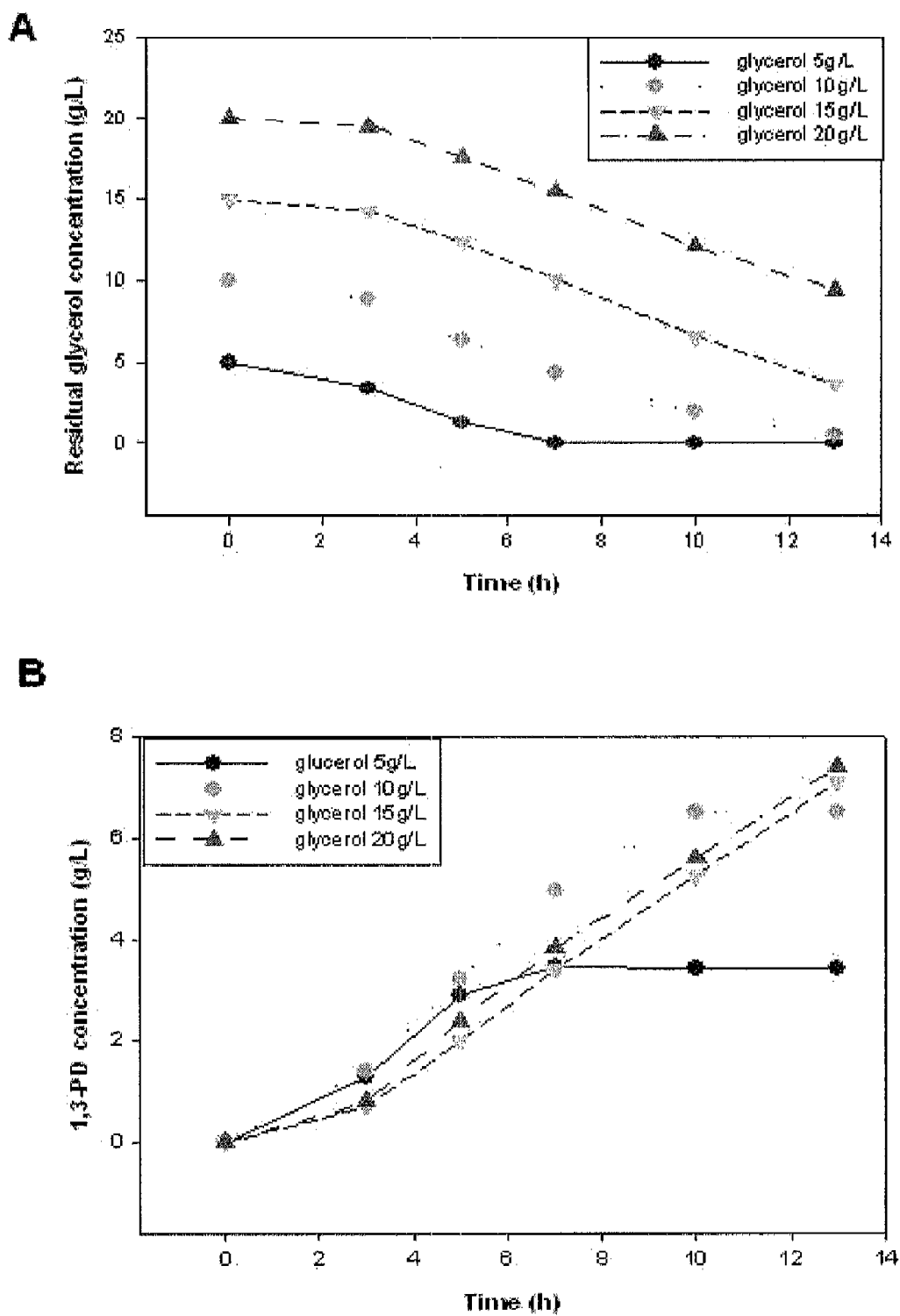
FIG. 13 shows the culture characteristics of the recombinant strain used in the present invention as a function of glycerol concentration.

The two-step culture of the AK-VOT strain was carried out under the same conditions as Example 4. When the $OD_{600}$ value (indicating the degree of growth of the strain) reached 2.0, glycerol was added to the culture broth to each of final concentrations of 5 g/L, 10 g/L, 15 g/L and 20 g/L. After 7 hours of culture, the production of 1,3-propanediol was compared between the glycerol concentrations. As a result, it was found that the strain showed the highest production of 1,3-propanediol (4.94 g/L) at an initial glycerol concentration of 10 g/L and also the highest glycerol-to-1,3-propanediol conversion rate (70%) at that glycerol concentration (FIG. 13 and Table 5).

TABLE 5

Results of fermentation at various glycerol concentrations

| Initial glycerol (g/L) | 5 | 10 | 15 | 20 |
|---|---|---|---|---|
| Residual glycerol (g/L) | 0 | 1.9 | 6.6 | 12.1 |
| 1,3-PD production (g/L) | 3.44 | 4.94 | 3.4 | 3.83 |
| Glycerol-to-1,3-PD conversion rate (%, mol/mol) | 0.49 | 0.70 | 0.49 | 0.55 |
| 1,3-PD productivity (g/Lh) | 0.83 | 0.73 | 0.49 | 0.59 |

Example 6

Effect of Aeration Rates

Figure 14:
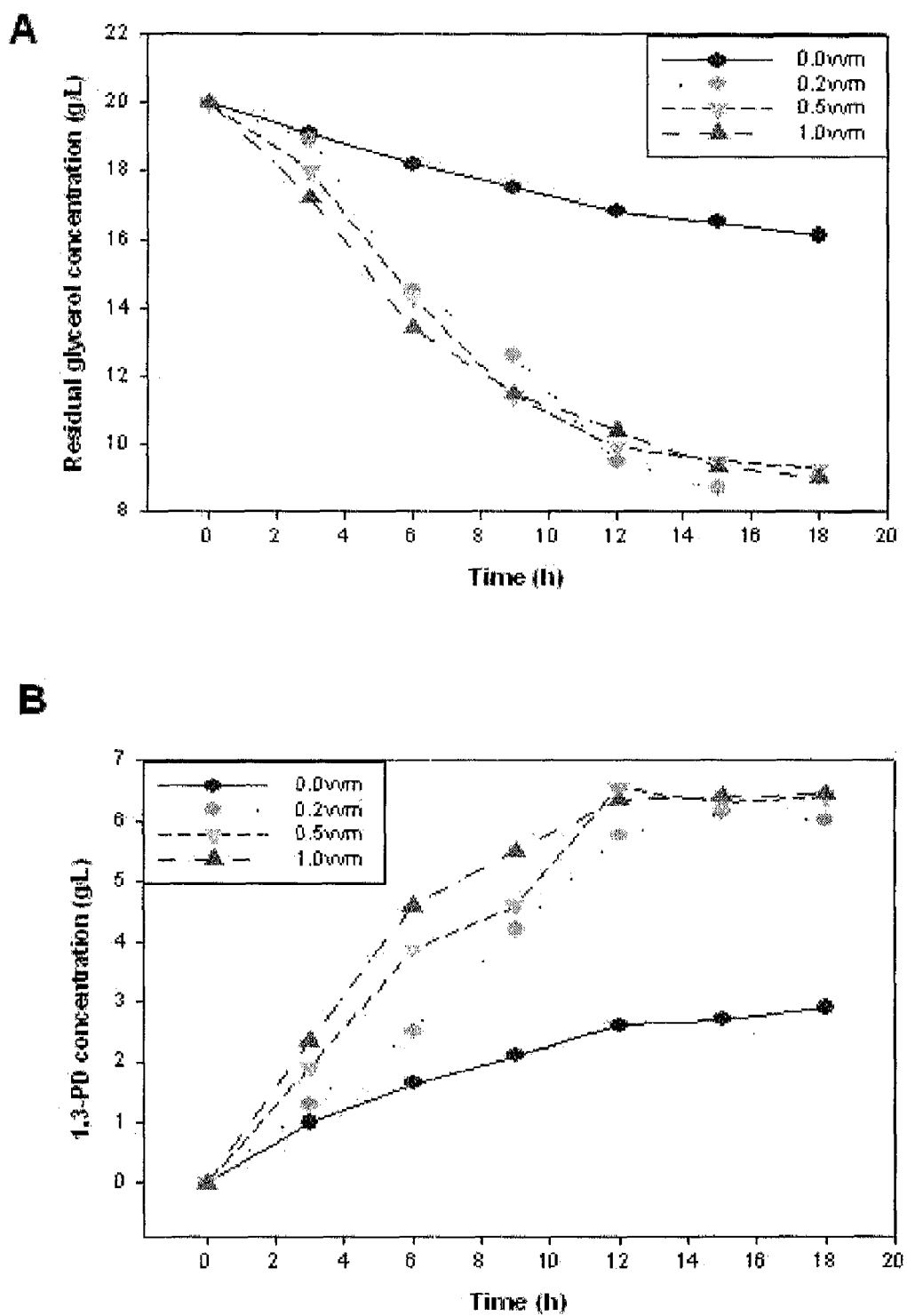
FIG. 14 shows the culture characteristics of the recombinant strain used in the present invention as a function of aeration rate.

The two-step culture of the AK-VOT strain was carried out under the same conditions as Example 4. When the $OD_{600}$ value (indicating the degree of growth of the strain) reached 2.0, glycerol was added to the culture broth to a final concentration of 20 g/L, and the culture of the strain was carried out at various aeration rates of 0.0 vvm, 0.2 vvm, 0.5 vvm and 1.0 vvm. As a result, as shown in FIG. 14, the strain consumed little or no glycerol at an aeration rate of 0.0 vvm, and the consumption of glycerol and the production of 1,3-propanediol were almost similar between aeration rates of 0.2 vvm, 0.5 vvm and 1.0 vvm.

Example 7

Effect of pH

Figure 15:
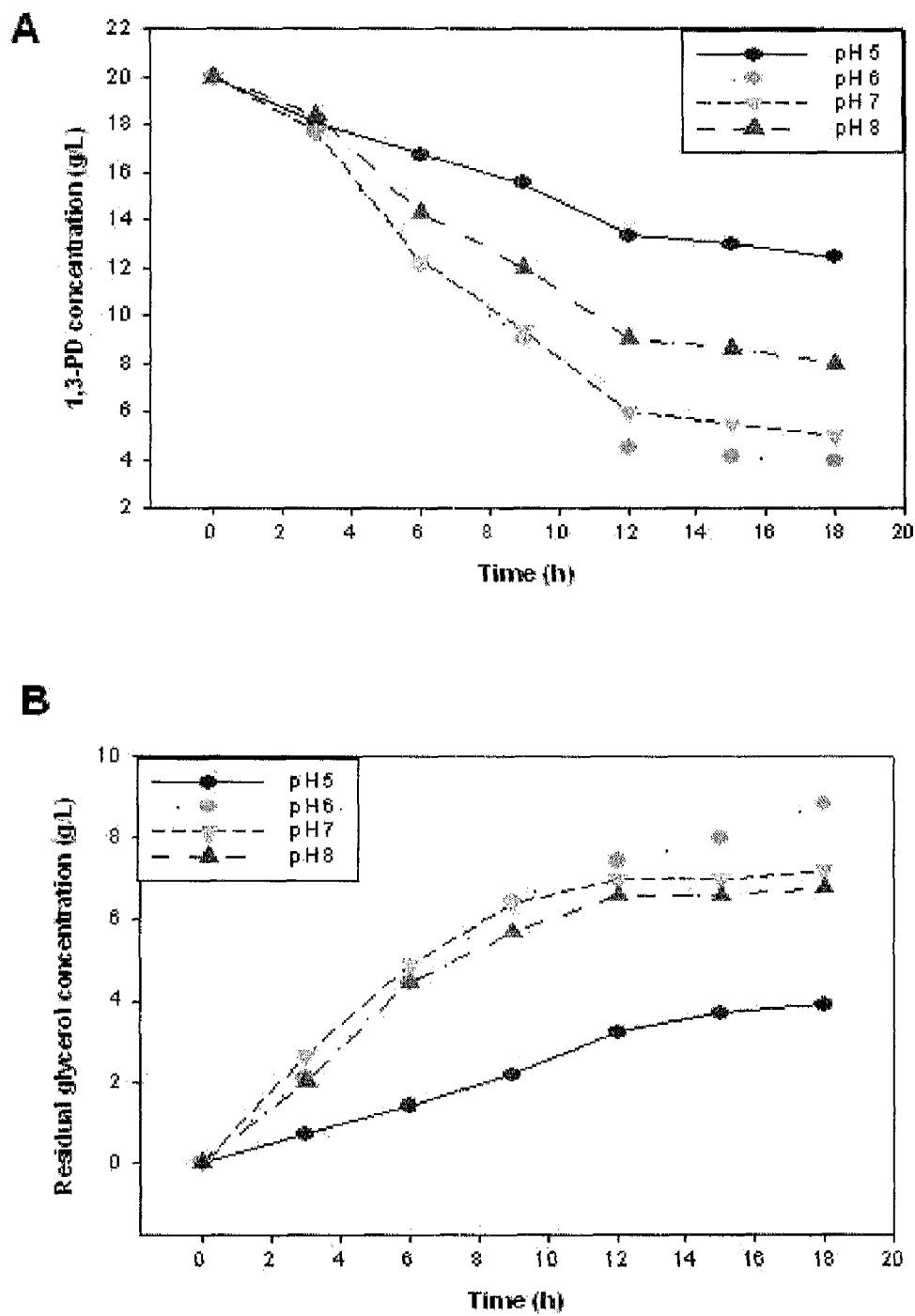
FIG. 15 shows the culture characteristics of the recombinant strain used in the present invention as a function of pH.

The two-step culture of the AK-VOT strain was carried out under the same conditions as Example 4. When the $OD_{600}$ value (indicating the degree of growth of the strain) reached 2.0, glycerol was added to the culture broth to a final concentration of 20 g/L, and the pH of the culture broth was maintained at each of pH values of 5, 6, 7 and 8 up to the end of the culture. As a result, as shown in FIG. 15, the strain showed the highest productivity of 1,3-propanediol at a pH of 6.

Example 8

Effect of Concentration of Microbial Cells

Figure 16:
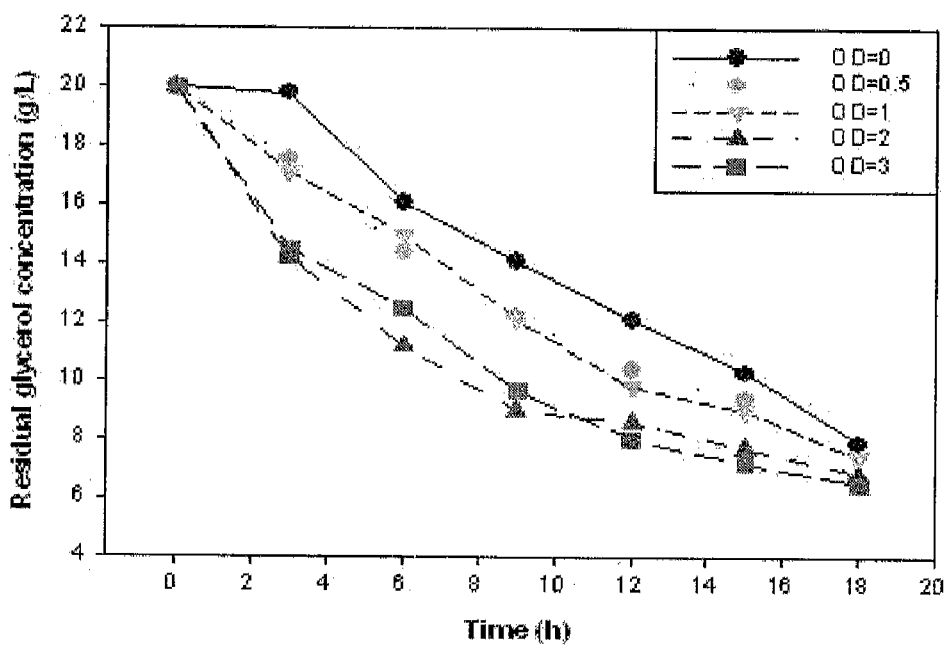
FIG. 16 shows the culture characteristics of the recombinant strain used in the present invention as a function of the amount of microbial cells.
Figure 16:
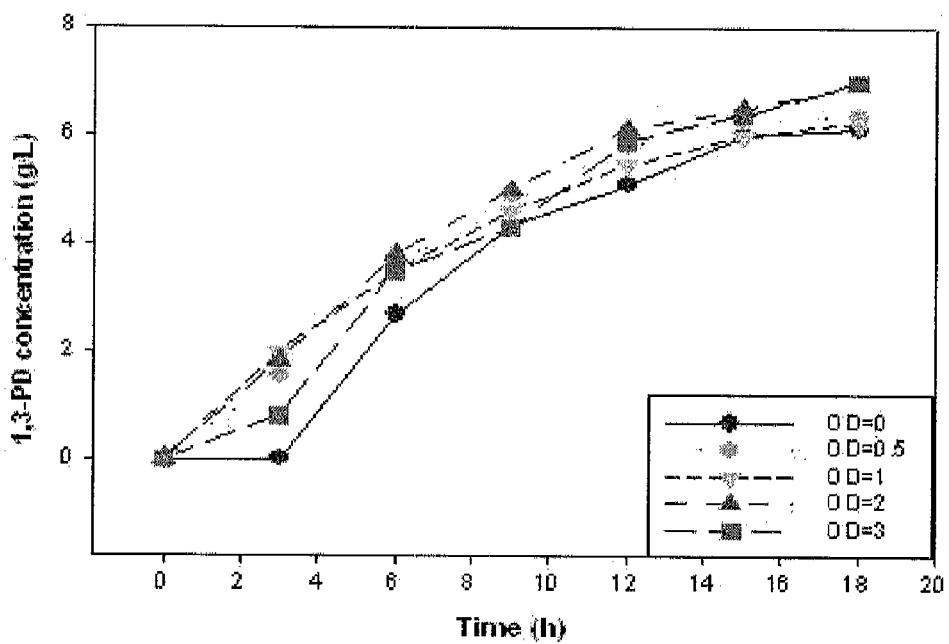

The two-step culture of the AK-VOT strain was carried out under the same conditions as Example 4. When the $OD_{600}$ value (indicating the degree of growth of the strain) reached each of 0, 0.5, 1, 2 and 3, glycerol was added to the culture broth to a final concentration of 20 g/L. As a result, as can be seen in FIG. 16, the higher the $OD_{600}$ value, the higher was the productivity of 1,3-propanediol.

INDUSTRIAL APPLICABILITY

As described above, when the recombinant strain in which the glycerol oxidative pathway that produces byproducts had been blocked is cultured in two steps, 1,3-propanediol can be produced with improved yield without producing products that result in an increase in purification costs.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

SEQUENCE LISTING

The electronic file was attached.

What is claimed is:

1. A microbial mutant which has the ability to produce 1,3-propanediol using glycerol as a carbon source, in which the *Klebsiella pneumoniae* strain having Korean Collection for Type Cultures (KCTC) deposit number KCTC11419BP is transformed with a vector comprising a 1,3-propanediol oxidoreductase-encoding gene or in which the 1,3-propanediol oxidoreductase-encoding gene is inserted into the chromosome of the *Klebsiella pneumoniae* strain having KCTC deposit number KCTC11419BP.

2. A microbial mutant which has the ability to produce 1,3-propanediol using glycerol as a carbon source, in which the *Klebsiella pneumoniae* strain having KCTC deposit number KCTC11419BP is transformed with a vector comprising a 1,3-propanediol oxidoreductase-encoding gene and a glycerol dehydratase reactivation factor-encoding gene or in which the 1,3-propanediol oxidoreductase-encoding gene and the glycerol dehydratase reactivation factor-encoding gene are inserted into the chromosome of the *Klebsiella pneumoniae* strain having KCTC deposit number KCTC11419BP.

3. A microbial mutant which has the ability to produce 1,3-propanediol using glycerol as a carbon source, in which the *Klebsiella pneumoniae* strain having KCTC deposit number KCTC11420BP is transformed with a vector comprising a 1,3-propanediol oxidoreductase-encoding gene or in which the 1,3-propanediol oxidoreductase-encoding gene is inserted into the chromosome of the *Klebsiella pneumoniae* strain having KCTC deposit number KCTC11420BP.

4. A microbial mutant which has the ability to produce 1,3-propanediol using glycerol as a carbon source, in which the *Klebsiella pneumoniae* strain having KCTC deposit number KCTC11420BP is transformed with a vector comprising a 1,3-propanediol oxidoreductase-encoding gene and a glycerol dehydratase reactivation factor-encoding gene or in which the 1,3-propanediol oxidoreductase-encoding gene and the glycerol dehydratase reactivation factor-encoding gene are inserted into the chromosome of the Klebsiella pneumoniae strain having KCTC deposit number KCTC11420BP.

5. A method of producing 1,3-propanediol, the method comprising the steps of: producing 1,3-propanediol by culturing the microbial mutant of claim 1 in a glycerol-containing medium; and recovering the produced 1,3-propanediol.

6. A method of producing 1,3-propanediol by culturing the microbial mutant of claim 1, the method comprising the steps of:
    (a) culturing the microbial mutant in a glycerol-free culture medium to grow cells of the microbial mutant;
    (b) adding glycerol to the culture medium in which the microbial mutant cells have been grown, and further culturing the microbial mutant cells to produce 1,3-propanediol; and
    (c) recovering the produced 1,3-propanediol.

7. The method according to claim 6, wherein the glycerol is added at a concentration of 5-50 g/L.

8. A method of producing 1,3-propanediol by culturing the microbial mutant of claim 2, the method comprising the steps of:
    (a) culturing the microbial mutant in a glycerol-free culture medium to grow cells of the microbial mutant;
    (b) adding glycerol to the culture medium in which the microbial mutant cells have been grown, and further culturing the microbial mutant cells to produce 1,3-propanediol; and
    (c) recovering the produced 1,3-propanediol.

9. The method according to claim 8, wherein the glycerol is added at a concentration of 5-50 g/L.

10. A method of producing 1,3-propanediol by culturing the microbial mutant of claim 3, the method comprising the steps of:
    (a) culturing the microbial mutant in a glycerol-free culture medium to grow cells of the microbial mutant;
    (b) adding glycerol to the culture medium in which the microbial mutant cells have been grown, and further culturing the microbial mutant cells to produce 1,3-propanediol; and
    (c) recovering the produced 1,3-propanediol.

11. The method according to claim 10, wherein the glycerol is added at a concentration of 5-50 g/L.

12. A method of producing 1,3-propanediol by culturing the microbial mutant of claim 4, the method comprising the steps of:
    (a) culturing the microbial mutant in a glycerol-free culture medium to grow cells of the microbial mutant;
    (b) adding glycerol to the culture medium in which the microbial mutant cells have been grown, and further culturing the microbial mutant cells to produce 1,3-propanediol; and
    (c) recovering the produced 1,3-propanediol.

13. The method according to claim 12, wherein the glycerol is added at a concentration of 5-50 g/L.

14. A method of producing 1,3-propanediol, the method comprising the steps of: producing 1,3-propanediol by culturing the microbial mutant of claim 2 in a glycerol-containing medium; and recovering the produced 1,3-propanediol.

15. A method of producing 1,3-propanediol, the method comprising the steps of: producing 1,3-propanediol by culturing the microbial mutant of claim 3 in a glycerol-containing medium; and recovering the produced 1,3-propanediol.

16. A method of producing 1,3-propanediol, the method comprising the steps of: producing 1,3-propanediol by culturing the microbial mutant of claim 4 in a glycerol-containing medium; and recovering the produced 1,3-propanediol.

* * * * *